(12) United States Patent
Kuwata

(10) Patent No.: US 9,809,563 B2
(45) Date of Patent: Nov. 7, 2017

(54) MALEIC ACID SALT OF ANTI-PRION COMPOUND, METHOD FOR PRODUCING THE SAME AND PHARMACEUTICAL COMPOSITION OF THE SAME

(71) Applicant: GIFU University, Gifu (JP)

(72) Inventor: Kazuo Kuwata, Gifu (JP)

(73) Assignee: GIFU University, Gifu (JP)

( * ) Notice: Subject to any disclaimer, the term of this patent is extended or adjusted under 35 U.S.C. 154(b) by 0 days.

(21) Appl. No.: 15/114,494

(22) PCT Filed: Feb. 3, 2015

(86) PCT No.: PCT/JP2015/052982
§ 371 (c)(1),
(2) Date: Sep. 8, 2016

(87) PCT Pub. No.: WO2015/119111
PCT Pub. Date: Aug. 13, 2015

(65) Prior Publication Data
US 2016/0368885 A1    Dec. 22, 2016

(30) Foreign Application Priority Data

Feb. 10, 2014  (JP) ................................. 2014-023838

(51) Int. Cl.
*C07D 295/15* (2006.01)
*C07C 57/145* (2006.01)

(52) U.S. Cl.
CPC .......... *C07D 295/15* (2013.01); *C07C 57/145* (2013.01)

(58) Field of Classification Search
None
See application file for complete search history.

(56) References Cited

FOREIGN PATENT DOCUMENTS

| JP | 2005120002 A | 5/2005 |
|---|---|---|
| JP | 2009013126 A | 1/2009 |

(Continued)

OTHER PUBLICATIONS

Berge et al., Journal of Pharmaceutical Sciences, vol. 66, No. 1, pp. 1-19.*

(Continued)

*Primary Examiner* — Karl J Puttlitz
(74) *Attorney, Agent, or Firm* — Marshall, Gerstein & Borun LLP

(57) ABSTRACT

An object of the present invention is to provide an anti-prion compound that has high crystallinity and is highly stable in the crystalline form and to provide a medicament for preventing, ameliorating or treating a prion disease. The present invention provides a maleic acid salt of a compound represented by formula (1):

(1)

4 Claims, 9 Drawing Sheets

(56) References Cited

FOREIGN PATENT DOCUMENTS

| JP | 2011063574 A | | 3/2011 |
|---|---|---|---|
| WO | 2010131717 | * | 11/2010 |
| WO | WO-2010131717 A1 | | 11/2010 |

OTHER PUBLICATIONS

Handbook of Pharmaceutical Salts Properties, Selection, and Use 1st Edition by P. Heinrich Stahl (Editor), Camille G. Wermuth (Editor), Wiley VCH, 2002, pp. 330-345.*
Prusiner et al., Proc Natl Acad Sci U S Av.112(38); Sep. 22, 2015.*
Machine Translation of WO 2010131717 on Google Patents; 2010.*
Kimura et al., "Synthesis of GN8 derivatives and evaluation of their antiprion activity in TSE-infected cells", Bioorganic & Medicinal Chemistry Letters 21, pp. 1502-1507 (2011).
Kuwata et al., "Hot spots in prion protein for pathogenic conversion", PNAS, vol. 104, No. 29, pp. 11921-11926 (Jul. 17, 2007).
International Search Report and Written Opinion for Application No. PCT/JP2015/052982, dated Apr. 21, 2015.
International Preliminary Report on Patentability for International Application No. PCT/JP2015/052982, dated Aug. 16, 2016. (English Translation).

* cited by examiner

MALEIC ACID SALT OF ANTI-PRION COMPOUND, METHOD FOR PRODUCING THE SAME AND PHARMACEUTICAL COMPOSITION OF THE SAME

TECHNICAL FIELD

The present invention relates to a novel maleic acid salt of an anti-prion compound, a method for producing the same, and a medicament for preventing, ameliorating or treating a prion disease, comprising the same.

BACKGROUND ART

Prion diseases are fatal neurodegenerative disorders characterized by the accumulation of an abnormal isoform of prion protein in the brain. The development of therapeutic drugs for prion diseases directly relates to therapy for human prion diseases, such as Creutzfeldt-Jakob disease, and will significantly contribute to medical care including community medicine. Such therapeutic drugs for prion diseases can also be used as a BSE prevention medicine for animals including humans and domestic and companion animals.

No effective therapy for prion diseases has been developed and thus there has been a demand for prompt discovery of a new therapeutic drug for prion diseases. A number of compounds have been identified that inhibit prion in prion-infected cells (anti-prion compounds), these compounds are inadequate for use as clinical therapeutic drugs for the following reasons: (1) their anti-prion activity is not sufficient, (2) their molecular structure is unsuitable for optimization, (3) their low blood-brain barrier permeability resulting in low anti-prion effect in vivo, in particular, in the brain, which is the organ mainly affected by prion diseases, and (4) their adverse effects, such as hepatic dysfunction.

The inventor discovered novel anti-prion compounds, including the compounds described in Non-Patent Literature 1, and the compounds with higher activity described in Patent Literature 1. The compounds described in Patent Literature 1 were found to be highly effective for the prevention of onset and progression of prion diseases.

However, conventional anti-prion compounds, including those described in Non-Patent Literature 1 and Patent Literature 1, have poor crystallinity and are unstable in the crystalline form. Due to such lack of high purity or storage stability, these compounds are difficult to be clinically applied as medicaments.

CITATION LIST

Patent Literature

Patent Literature 1: WO 2010/131717

Non-Patent Literature

Non-Patent Literature 1: Proc. Natl. Acad. Sci. U.S.A. 2007, 104, 11921.

SUMMARY OF INVENTION

Technical Problem

The present invention has been made to solve the above problems, and an object of the present invention is thus to provide an anti-prion compound that has high crystallinity and is highly stable in the crystalline form and to provide a highly applicable medicament for preventing, ameliorating or treating a prion disease.

Solution to Problem

The inventor conducted extensive studies to solve the above problems and, as a result, found that a maleic acid salt of a compound represented by formula (1) below surprisingly has higher crystallinity and higher long-term stability in the crystalline form, as compared with other types of inorganic and organic acid salts of the compound of formula (1). The inventor further found that the maleic acid salt can be advantageously synthesized at an industrial large-scale.

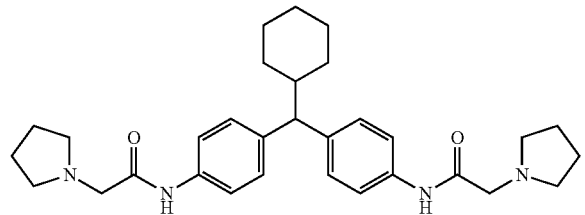

(1)

The inventor also found other unexpected findings as described later. The inventor further investigated research and completed the present invention.

That is, the present invention relates to an invention comprising the maleic acid salt as an essential component as described below.

[1] A maleic acid salt of a compound represented by formula (1):

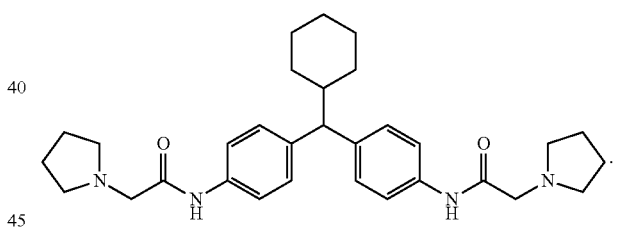

(1)

[2] A pharmaceutical composition comprising the maleic acid salt of the above [1] as an active ingredient.

[3] The pharmaceutical composition of the above [2], which is a medicament for preventing, ameliorating or treating a prion disease.

[4] The pharmaceutical composition of the above [2] or [3], wherein the maleic acid salt of the above [1] shows a retention rate of 97% or more after 30-day storage in the form of an aqueous solution at a concentration of 25% w/v.

[5] A method for producing the maleic acid salt of the above [1], the method comprising bringing the compound of formula (1) of the above [1] in contact with maleic acid.

[6] The pharmaceutical composition of any one of the above [2] to [4], which is a preparation that reaches the brain.

Advantageous Effects of Invention

The present invention enables the production of an anti-prion compound that has high crystallinity and is stable in the crystalline form. The anti-prion compound can be advantageously synthesized at an industrial large scale.

The compound of formula (1) in a free form is poorly soluble in water and thus an effective water-soluble preparation of the compound is difficult to produce. In contrast, the anti-prion compound of the present invention has excellent water solubility, and can be intravenously administered or used as an injection.

The present invention thus provides a clinically applicable therapeutic drug for a prion disease.

DESCRIPTION OF EMBODIMENTS

Figure 1:
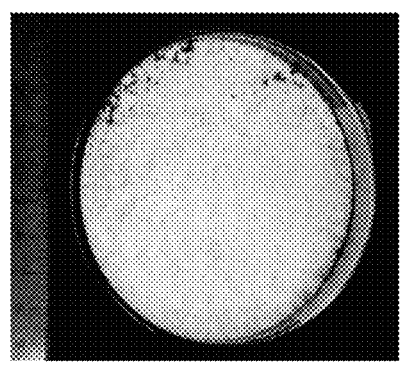
FIG. 1 shows a photograph of a maleic acid salt after two-week stress testing in Example 2.

The present invention will be described in detail below.

The present invention provides a maleic acid salt of a compound represented by formula (1):

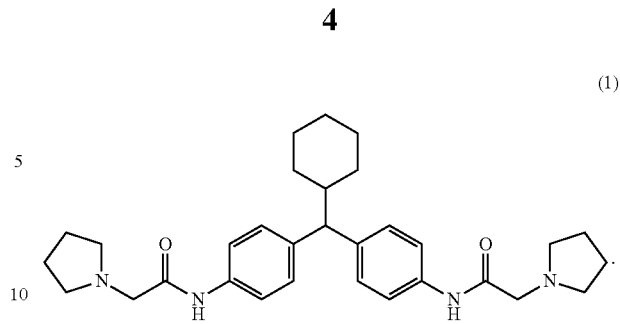

The maleic acid salt of the present invention surprisingly has higher crystallinity in terms of quality and quantity as well as higher stability in the crystalline form, as compared with the corresponding salts of formula (1) formed by addition of an inorganic or organic acid (for example, hydrochloric acid, sulfuric acid, phosphoric acid, citric acid, malic acid, tartaric acid, acetic acid, lactic acid, salicylic acid, mandelic acid, fumaric acid or benzene-sulfonic acid).

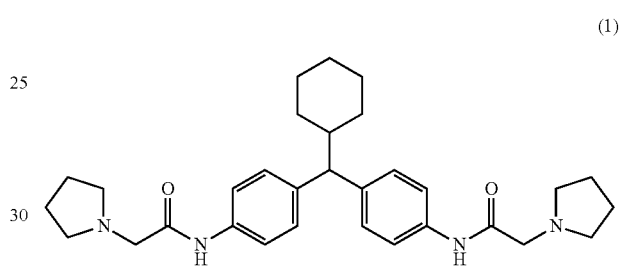

The maleic acid salt of the present invention can be synthesized by, for example, the method described below, but the present invention is not limited thereto. The production method described below is particularly preferred and industrially advantageous because the method does not introduce any impurities that hinder the formation of the maleic acid salt of the present invention.

Preferred Production Method

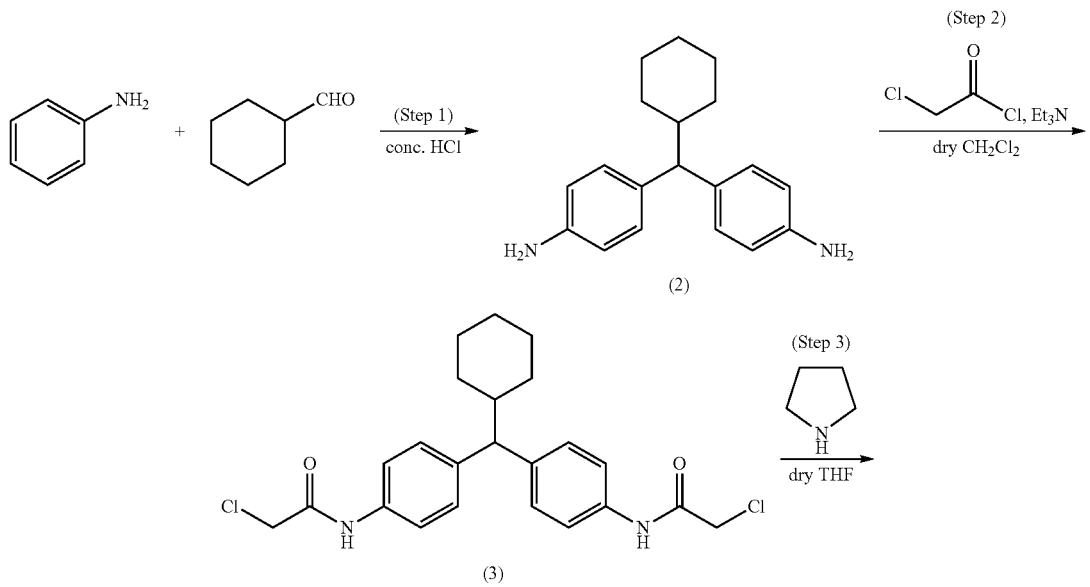

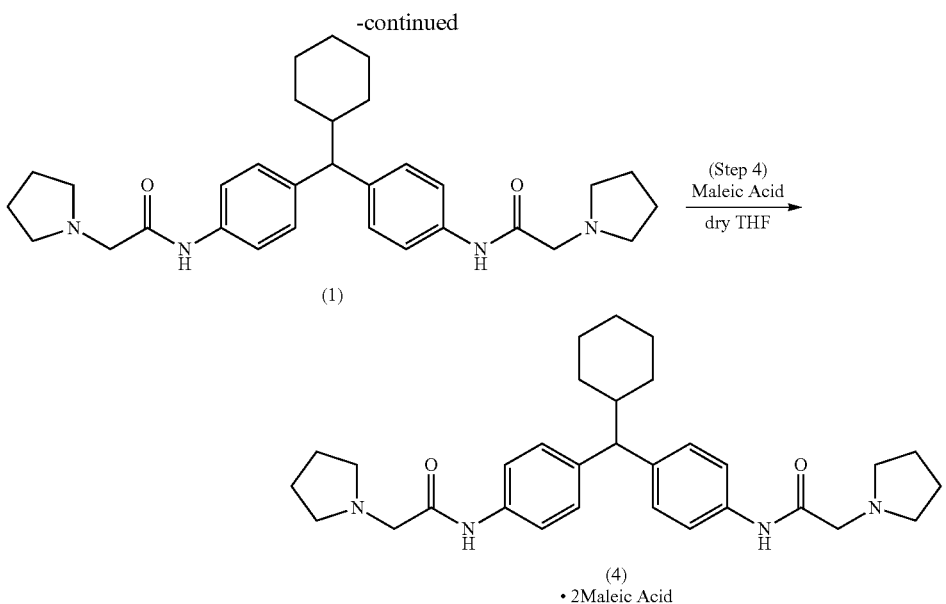

(In the formulae, conc. HCl represents concentrated hydrochloric acid, THF represents tetrahydrofuran, Et represents ethyl, dry represents a drying process, and Maleic Acid represents maleic acid. The same applies hereinafter.)

The reactions in steps 1 to 4 can be performed in the presence or absence of a solvent. The solvent used in the synthesis of the maleic acid salt of the present invention is not specifically limited.

Examples of the solvent include aromatic hydrocarbons such as benzene, toluene, xylene and ethyl benzene; halogenated hydrocarbons such as chloroform, dichloromethane and 1,2-dichloroethane; ethers such as diethyl ether, dimethoxyethane, tetrahydrofuran (THF) and dioxane; esters such as methyl acetate, ethyl acetate, isopropyl acetate and butyl acetate; amides such as N,N-dimethylformamide and N,N-dimethylacetamide; and nitriles such as acetonitrile, propionitrile and benzonitrile. These solvents can be used alone or as a mixture of two or more types thereof.

The reactions in steps 1 to 4 can be performed under normal pressure or elevated pressure.

After completion of each reaction, the reaction product may be isolated from the reaction system by a conventional procedure. The reaction product may be isolated and/or purified by a conventional procedure including, as necessary, for example, pH adjustment, filtration, concentration, crystallization, washing, recrystallization, extraction, distillation, sublimation purification, column chromatography and vacuum drying. The reaction product may be subjected to the next step without isolation, separation or purification.

Examples of the solvent used for recrystallization (crystallization) of the reaction product in steps 1 to 4 include water; alcohols such as methanol, ethanol, 1-propanol, isopropanol and 1-pentanol; acetone; acetonitrile; tetrahydrofuran (THF); and ethers such as cyclopentyl methyl ether (CPME) and diisopropyl ether.

Production in Step 1

Cyclohexanecarboxaldehyde can be reacted with aniline in the presence of an acid such as concentrated hydrochloric acid to give 4,4'-(cyclohexylmethylene)dianiline represented by formula (2).

Examples of the acid used in the reaction include concentrated hydrochloric acid and sulfuric acid, and preferred is concentrated hydrochloric acid. The amount of the acid used may vary depending on the scale of the reaction, the reaction temperature, etc., but is usually appropriately selected from the range of about 0.05 to 0.3 mol, and is preferably about 0.05 to 0.15 mol and more preferably about 0.10 to 0.13 mol, relative to 1 mol of cyclohexanecarboxaldehyde.

The amount of aniline used in the reaction may vary depending on the scale of the reaction, the reaction temperature, etc., but is usually appropriately selected from the range of about 2.0 to 5.0 mol, and is preferably about 3.0 to 4.5 mol and more preferably about 3.9 to 4.3 mol, relative to 1 mol of cyclohexanecarboxaldehyde.

The reaction temperature in the reaction can be appropriately selected depending on the scale of the reaction etc., but usually the internal temperature of the reaction mixture is required to be within the range of about 120 to 150° C., and is preferably about 130 to 140° C.

The reaction time in the reaction may vary depending on the scale of the reaction, the reaction temperature, etc., but is usually appropriately selected within the range of several minutes to about 7 hours, and is preferably about 4 to 7 hours, and more preferably about 5 to 6 hours. The term "several minutes" refers to about 1 to 10 minutes.

Production in Step 2

N,N'-[(cyclohexylmethylene)di-4,1-phenylene]bis(2-chloroacetamide) of formula (3) can be produced by reacting 4,4'-(cyclohexylmethylene)dianiline of formula (2) with chloroacetyl chloride preferably in the presence of a base and a solvent.

Instead of N,N'-[(cyclohexylmethylene)di-4,1-phenylene]bis(2-chloroacetamide) of formula (3), N,N'-[(cyclohexylmethylene)di-4,1-phenylene]bis(2-bromoacetamide) may be produced. In this case, bromoacetyl bromide may be used instead of chloroacetyl chloride.

Examples of the base used in the reaction include triethylamine, potassium carbonate, sodium carbonate, pyridine, N,N-dimethyl-4-aminopyridine, 1,4-diazabicyclo[2,2,2]octane and N,N-diisopropylethylamine, and preferred is triethylamine. The amount of the base used may vary depending on the scale of the reaction, the reaction temperature, etc., but is usually appropriately selected from the range of about 2.0 to 3.0 mol, and is preferably about 2.15 to 2.17 mol, relative to 1 mol of 4,4'-(cyclohexylmethylene)dianiline of formula (2).

The solvent used in the reaction is preferably dichloromethane, chloroform, or CPME. The amount of the solvent used is not limited to a specific amount, but is usually appropriately selected from the range of an about 1.0- to 45-fold amount, and is preferably an about 40- to 50-fold amount and more preferably an about 44- to 46-fold amount, relative to 1 part by weight of 4,4'-(cyclohexylmethylene)dianiline of formula (2).

The amount of chloroacetyl chloride used in the reaction may vary depending on the scale of the reaction, the reaction temperature, etc., but is usually appropriately selected from the range of about 2.0 to 3.0 mol, and is preferably about 2.17 to 2.20 mol, relative to 1 mol of 4,4'-(cyclohexylmethylene)dianiline of formula (2).

The reaction temperature in the reaction can be appropriately selected depending on the scale of the reaction etc., but usually the internal temperature of the reaction mixture is required to be within the range of about −4 to 0° C., and is preferably about −4 to −1° C.

The reaction time in the reaction may vary depending on the scale of the reaction, the reaction temperature, etc., but is usually appropriately selected within the range of several minutes to about 20 hours, and is preferably about 15 to 20 hours, and more preferably about 16 to 18 hours.

Production in Step 3

N,N'-[(cyclohexylmethylene)di-4,1-phenylene]bis[2-(1-pyrrolidinyl)acetamide] of formula (1) can be produced by reacting N,N'-[(cyclohexylmethylene)di-4,1-phenylene]bis(2-chloroacetamide) of formula (3) with pyrrolidine preferably in the presence of a solvent. Instead of N,N'-[(cyclohexylmethylene)di-4,1-phenylene]bis(2-chloroacetamide) of formula (3), N,N'-[(cyclohexylmethylene)di-4,1-phenylene]bis(2-bromoacetamide) may be used.

The amount of the pyrrolidine used in the reaction may vary depending on the scale of the reaction, the reaction temperature, etc., but is usually appropriately selected from the range of about 2.0 to 5.0 mol, and is preferably about 4.0 to 5.0 mol and more preferably about 4.4 to 4.6 mol, relative to 1 mol of N,N'-[(cyclohexylmethylene)di-4,1-phenylene]bis(2-chloroacetamide) of formula (3).

The solvent used in the reaction is preferably THF, ethyl acetate, diisopropyl ether, benzene, diethyl ether, or toluene. The amount of the solvent used in the reaction is not limited to a specific amount, but is usually appropriately selected from the range of an about 1.0- to 55.0-fold amount, and is preferably an about 50- to 55-fold amount and more preferably an about 51.7- to 53.0-fold amount, relative to 1 part by weight of N,N'-[(cyclohexylmethylene)di-4,1-phenylene]bis(2-chloroacetamide) of formula (3).

The reaction temperature in the reaction can be appropriately selected depending on the scale of the reaction etc., but usually the internal temperature of the reaction mixture is required to be within the range of about 22 to 28° C., and is preferably about 25 to 26° C.

The reaction time in the reaction may vary depending on the scale of the reaction, the reaction temperature, etc., but is usually appropriately selected within the range of several minutes to about 20 hours, and is preferably about 15 to 20 hours, and more preferably about 17 to 19 hours.

Production in Step 4

N,N'-[(cyclohexylmethylene)di-4,1-phenylene]bis[2-(1-pyrrolidinyl)acetamide] maleate of formula (4) can be produced by reacting N,N'-[(cyclohexylmethylene)di-4,1-phenylene]bis[2-(1-pyrrolidinyl)acetamide] of formula (1) with maleic acid in the presence of a solvent.

The solvent used in the reaction is preferably THF, diethyl ether, ethyl acetate, benzene, or toluene. The amount of the solvent used in the reaction is not limited to a specific amount, but is usually appropriately selected from the range of an about 1.0- to 130-fold amount, and is preferably an about 120- to 130-fold amount and more preferably an about 125- to 129-fold amount, relative to 1 part by weight of N,N'-[(cyclohexylmethylene)di-4,1-phenylene]bis[2-(1-pyrrolidinyl)acetamide] of formula (1).

The amount of the maleic acid used in the reaction may vary depending on the scale of the reaction, the reaction temperature, etc., but is usually appropriately selected from the range of about 2.0 to 3.0 mol, and is preferably about 2.2 to 2.5 mol, relative to 1 mol of N,N'-[(cyclohexylmethylene)di-4,1-phenylene]bis[2-(1-pyrrolidinyl)acetamide] of formula (1).

The reaction temperature in the reaction can be appropriately selected depending on the scale of the reaction etc., but usually the internal temperature of the reaction mixture is required to be within the range of about 0 to 30° C., and is preferably about 20 to 30° C., and more preferably about 25 to 26° C.

The reaction time in the reaction may vary depending on the scale of the reaction, the reaction temperature, etc., but is usually appropriately selected within the range of several minutes to about 5 hours, and is preferably about 3 to 5 hours, and more preferably about 4.0 to 4.5 hours.

Each reaction may be followed by a known procedure selected as appropriate, such as extraction, dissolution in a different solvent, concentration, chromatography, crystallization and recrystallization, and thereby the salt of the present invention can easily be obtained.

The maleic acid salt of the present invention has good anti-prion activity. The anti-prion activity herein refers to inhibitory activity against the formation of an abnormal isoform of prion protein.

The maleic acid salt of the present invention strongly binds to a normal form of prion protein, thereby inhibiting a conformational change of the normal form of prion protein into an abnormal isoform of prion protein. In this manner, the maleic acid salt exhibits good anti-prion activity.

Thus the maleic acid salt of the present invention can be used to inhibit such a conformational change of a normal form of prion protein and to prevent, ameliorate or treat a prion disease. The maleic acid salt of the present invention can be administered in an effective amount to a patient with a prion disease, thereby preventing, ameliorating or treating the prion disease.

The maleic acid salt of the present invention can be added to a food, such as steak or meat, a drink, etc. Accordingly, the present invention also provides a food, a food additive, etc. comprising the compound of the present invention.

The term "normal form of prion protein" herein refers to a non-infectious form of prion protein that is expressed in normal cells. The term "abnormal isoform of prion protein" herein refers to an infectious isoform of prion protein with the same amino acid sequence as that of a normal form of prion protein, but with a different conformation. The phrase "infected with prion" means that a normal form of prion protein has undergone a conformational change into an abnormal isoform of prion protein.

The prion disease herein refers to a disease caused by an abnormal isoform of prion protein resulting from a conformational change of a normal form of prion protein. Examples of the prion disease include scrapie in sheep, bovine spongiform encephalopathy, Creutzfeldt-Jakob disease, GSS, FFI, kuru and variant Creutzfeldt-Jakob disease.

The term "preventing" herein includes the prevention or delaying of the onset of a disease, and the reduction in the incidence rate. The terms "ameliorating" and "treating" herein include the alleviation of the symptoms, the prevention of the progression of the symptoms, and the cure or complete removal of a disease.

Pharmaceutical Compositions

The present invention includes a pharmaceutical composition comprising the maleic acid salt of the present invention as an active ingredient.

The pharmaceutical composition of the present invention preferably serves as a medicament for preventing, ameliorating or treating a prion disease. The pharmaceutical composition of the present invention can be administered to humans or non-human mammals (for example, rats, mice, rabbits, sheep, pigs, cattle, cats, dogs, monkeys, etc.).

The method for producing the pharmaceutical composition of the present invention is not specifically limited as long as the method uses the maleic acid salt of the present invention as an ingredient. The pharmaceutical composition can be produced in accordance with a conventionally known method.

The pharmaceutical composition of the present invention is preferably a preparation that reaches the brain.

The dosage form of the pharmaceutical composition of the present invention is not specifically limited, and examples thereof include liquid preparations such as injections, creams, ointments, drinks, aerosols, gels for cutaneous application, eye drops and nasal drops; and solid preparations such as tablets, capsules, powders, granules, controlled-release dosage forms and suppositories. Preferred is a dosage form that is easily administered to a patient with a prion disease, and examples thereof include an injection, a tablet, etc. The injection may be an aqueous injection or an oily injection.

The liquid preparation such as an injection is desirably stored after removal of moisture by freeze-drying or lyophilization. A lyophilized preparation is redissolved in distilled water for injection at the time of use.

The pharmaceutical composition of the present invention in any suitable dosage form may contain, in addition to the maleic acid salt of the present invention, a pharmaceutically acceptable vehicle or carrier, a pharmaceutically acceptable additive, a physiologically active or pharmacologically active substance other than the maleic acid salt of the present invention, etc.

The pharmaceutical composition of the present invention in any suitable dosage form may be used as a food product, a food additive, a supplement or a health food, and can be usually packaged in a container or a sachet by a conventional procedure. The container or sachet is not specifically limited as long as the container or sachet can be used for packaging a food product, a supplement, a medicament, a health food, etc. The container or sachet is appropriately selected from conventionally known containers or sachets, depending on the dosage form of the pharmaceutical composition of the present invention.

The physical state of the pharmaceutical composition of the present invention is not specifically limited, and examples thereof include liquid, fluid, gel, semi-solid and solid. The physical state of the pharmaceutical composition also include a liquid, fluid, gel, semi-solid, or solid state resulting from preparation before use.

The amount of the maleic acid salt of the present invention contained in the pharmaceutical composition of the present invention is usually about 0.01 to 0.12% by weight, preferably about 0.02 to 0.10% by weight, and more preferably about 0.02 to 0.05% by weight based on the total amount of the pharmaceutical composition. The maleic acid salt in such an amount sufficiently exerts the effect of preventing, ameliorating or treating a prion disease.

The mode of administration of the pharmaceutical composition of the present invention is not specifically limited and may be oral administration or parenteral administration. The pharmaceutical composition can be systemically or topically administered through, for example, intraarterial, intravenous, intramuscular, subcutaneous, intraperitoneal, intrarectal, transpulmonary, transdermal, transnasal, or intraocular administration.

Preferred modes of administration are intravenous administration etc.

The dosage of the pharmaceutical composition of the present invention is appropriately selected depending on the mode of administration, the dosage form, the species, age, body weight, medical history, etc. of the subject to which the composition is to be administered, etc. The dosage of the composition is usually about 1.0 to 500 mg, preferably about 10 to 100 mg, per kg of body weight as a single dose.

The frequency of administration is also appropriately selected depending on the dosage form, the severity of the prion disease, the age etc. of the subject, etc. The pharmaceutical composition may be administered in a single dose or continuously infused in multiple doses with certain intervals. In the case of continuous infusion, the frequency of administration may be once a day to once in several months.

The vehicle or carrier used in the pharmaceutical composition of the present invention is not specifically limited, and examples thereof include aqueous solvents such as water and a polar solvent; polyhydric alcohols; vegetable oils; and oily vehicles. Examples of the vehicle or carrier used in the injection include distilled water for injection and physiological saline.

These vehicles or carriers can be used alone or in combination of two or more types.

Examples of the pharmaceutically acceptable additive used in the pharmaceutical composition of the present invention include a surfactant, a flavor or a cooling agent, an antiseptic, a bactericide or an antibacterial agent, a pH adjusting agent, an isotonic agent, a chelating agent, a buffering agent, a stabilizer, an antioxidant and a thickener. These additives can be used alone or in combination of two or more types.

Specific examples of the pharmaceutically acceptable additive will be listed below.

Examples of the surfactant include nonionic surfactants such as polyoxyethylene (hereinafter sometimes referred to as "POE")-polyoxypropylene (hereinafter sometimes referred to as "POP") block copolymers (for example, poloxamer 407, poloxamer 235 and poloxamer 188), POE-POP block copolymer adducts of ethylenediamine (for example, poloxamine), POE sorbitan fatty acid esters (for example, polysorbate 20, polysorbate 60 and polysorbate 80 (e.g., TO-10 etc.)), POE hardened castor oils (for example, POE (60) hardened castor oils (e.g., HCO-60 etc.)), POE castor oils, POE alkyl ethers (for example, polyoxyethylene (9) lauryl ether and polyoxyethylene (20) polyoxypropylene (4) cetyl ether) and polyoxyl stearate; zwitterionic surfactants such as glycine-type zwitterionic surfactants (for example, alkyldiaminoethylglycine and alkylpolyaminoethylglycine) and betaine-type zwitterionic surfactants (for example, lauryldimethylaminoacetic acid betaine and imidazolinium betaine); and cationic surfactants such as alkyl quaternary ammonium salts (for example, benzalkonium chloride and benzethonium chloride). The numbers in the parentheses represent the mole number of the POE or POP added.

Examples of the flavor or cooling agent include essential oils such as camphor, borneol, terpenes (these may be in the d-form, l-form, or dl-form), mentha water, eucalyptus oil, bergamot oil, anethole, eugenol, geraniol, menthol, limonene, mentha oil, peppermint oil and rose oil.

Examples of the antiseptic, bactericide or antibacterial agent include polidronium chloride, alkyldiaminoethylglycine hydrochloride, sodium benzoate, ethanol, benzalkonium chloride, benzethonium chloride, chlorhexidine gluconate, chlorobutanol, sorbic acid, potassium sorbate, sodium dehydroacetate, methyl parahydroxybenzoate, ethyl parahydroxybenzoate, propyl parahydroxybenzoate, butyl parahydroxybenzoate, oxyquinoline sulfate, phenethyl alcohol, benzyl alcohol, biguanide compounds (in particular, polyhexamethylene biguanide or its hydrochloric acid salt, etc.) and Glokill (Rhodia S.A.).

Examples of the pH adjusting agent include hydrochloric acid, sodium hydroxide, potassium hydroxide, calcium hydroxide, magnesium hydroxide, triethanolamine, monoethanolamine, diisopropanolamine, sulfuric acid and phosphoric acid.

Examples of the isotonic agent include sodium hydrogen sulfite, sodium sulfite, potassium chloride, calcium chloride, sodium chloride, magnesium chloride, potassium acetate, sodium acetate, sodium hydrogen carbonate, sodium carbonate, sodium thiosulfate, magnesium sulfate, disodium hydrogen phosphate, sodium dihydrogen phosphate, potassium dihydrogen phosphate, glycerol and propylene glycol.

Examples of the chelating agent include ascorbic acid, tetrasodium edetate, sodium edetate and citric acid.

Examples of the buffering agent include phosphate buffering agents; citrate buffering agents such as citric acid and sodium citrate; acetate buffering agents such as acetic acid, potassium acetate and sodium acetate; carbonate buffering agents such as sodium hydrogen carbonate and sodium carbonate; borate buffering agents such as boric acid and borax; and amino acid buffering agents such as taurine, aspartic acid and salts thereof (e.g., potassium salts) and epsilon-aminocaproic acid.

Examples of the stabilizer include trometamol, sodium formaldehyde sulfoxylate (rongalit), tocopherol, sodium pyrosulfite, monoethanolamine, aluminum monostearate and glyceryl monostearate.

Examples of the antioxidant include water-soluble antioxidants such as ascorbic acid, ascorbic acid derivatives (e.g., ascorbic acid-2-sulfate disodium salt, sodium ascorbate, ascorbic acid-2-phosphate magnesium salt and ascorbic acid-2-phosphate sodium salt), sodium hydrogen sulfite, sodium sulfite and sodium thiosulfate.

Examples of the thickener include guar gum; hydroxypropyl guar gum; cellulose polymers such as methylcellulose, ethylcellulose, hydroxypropyl methylcellulose, hydroxyethyl cellulose and carboxymethyl cellulose sodium; gum arabic; karaya gum; xanthan gum; agar-agar; alginic acid; α-cyclodextrin; dextrin; dextran; heparin; heparinoid; heparin sulfate; heparan sulfate; hyaluronic acid; salts of hyaluronic acid (e.g., sodium salts etc.); sodium chondroitin sulfate; starch; chitin and its derivatives; chitosan and its derivatives; carrageenan; sorbitol; polyvinyl polymers such as polyvinylpyrrolidone, polyvinyl alcohol and polyvinyl methacrylate; carboxy vinyl polymers such as alkali metal salts of polyacrylic acid (e.g., sodium salts, potassium salts, etc.), amine salts of polyacrylic acid (e.g., monoethanolamine salts, diethanolamine salts, triethanolamine salts, etc.), and ammonium salts of polyacrylic acid; casein; gelatin; collagen; pectin; elastin; ceramide; liquid paraffin; glycerol; polyethylene glycol; macrogol; alginic acid salts of polyethyleneimine (e.g., sodium salts etc.); alginic acid esters (e.g., propylene glycol ester etc.); powdered tragacanth and triisopropanolamine.

These additives can be used not only in the pharmaceutical composition of the present invention but also in the food product, the food additive, the health food and the supplement of the present invention.

Examples of the pharmacologically active or physiologically active substance other than the maleic acid salt in the pharmaceutical composition of the present invention include vitamins, amino acids, antibacterial drugs or bactericides, sugars, polymers, celluloses or their derivatives, and local anesthetics. Specific examples of these drugs will be listed below.

Examples of the vitamins include retinol acetate, retinol palmitate, pyridoxine hydrochloride, flavin adenine dinucleotide sodium, pyridoxal phosphate, cyanocobalamin, panthenol, calcium pantothenate, sodium pantothenate, ascorbic acid, tocopherol acetate, tocopherol nicotinate, tocopherol succinate, tocopherol calcium succinate and ubiquinone derivatives.

Examples of the amino acids include aminoethylsulfonic acid (taurine), glutamic acid, creatinine, sodium aspartate, potassium aspartate, magnesium aspartate, magnesium potassium aspartate, sodium glutamate, magnesium glutamate, epsilon-aminocaproic acid, glycine, alanine, arginine, lysine, γ-aminobutyric acid, γ-aminovaleric acid and sodium chondroitin sulfate. These amino acids may be in the d-form, l-form, or dl-form.

Examples of the antibacterial drugs or bactericides include alkylpolyaminoethylglycine, chloramphenicol, sulfamethoxazole, sulfisoxazole, sulfamethoxazole sodium, sulfisoxazole diethanolamine, sulfisoxazole monoethanolamine, sulfisoxazole sodium, sulfisomidine sodium, ofloxacin, norfloxacin, levofloxacin, lomefloxacin hydrochloride and acyclovir.

Examples of the sugars include monosaccharides and disaccharides, in particular, glucose, maltose, trehalose, sucrose, cyclodextrin, xylitol, sorbitol, and mannitol.

Examples of the polymers include alginic acid, sodium alginate, dextrin, dextran, pectin, hyaluronic acid, chondroitin sulfate, polyvinyl alcohol (completely or partially saponified products), polyvinylpyrrolidone, carboxy vinyl polymers, macrogol and pharmaceutically acceptable salts thereof.

Examples of the celluloses or their derivatives include ethylcellulose, hydroxyethyl cellulose, hydroxypropyl cellulose, hydroxypropyl methylcellulose, methylcellulose, carboxymethyl cellulose, sodium carboxymethyl cellulose, carboxyethyl cellulose and nitrocellulose.

Examples of local anesthetics include chlorobutanol, procaine hydrochloride and lidocaine hydrochloride.

Pharmacological Activity Testing

The testing of the pharmacological activity of the pharmaceutical composition of the present invention may be accomplished by any appropriate testing method that can assess an inhibitory activity against a conformational change of a normal form of prion protein. Typically, the pharmacological activity may be assessed by detecting the formation of an abnormal isoform of prion protein in prion-infected cells in the presence of a test substance. The prion-infected cells can be produced by allowing prion to infect cells susceptible to prion by a known method. The detection of an abnormal isoform of prion protein may be achieved by a known detection method for a specific protein, and preferred is a quantitative detection method. The quantitative detection method is usually performed by combining a means for recognizing a specific protein, such as an antibody, a nucleic acid and an analogue thereof (e.g., a peptide, a PNA, etc.), and a means for quantifying the recognized protein through, for example, image analysis involving labeling of the protein with a fluorescent substance, radiation, etc. (e.g., ELISA or ECL-plus Western blotting).

The pharmacological activity testing can be performed as follows, for example, prion is allowed to infect a mouse neural cell line, the cells are then cultured in culture medium containing a test substance (drug) at various concentrations for a certain period of time, the protein is collected, and an abnormal isoform of prion protein is detected with an antibody etc. and quantified by image analysis etc. In such a pharmacological activity testing, a smaller amount of the formation of an abnormal isoform of prion protein indicates higher inhibitory activity against a conformational change of prion protein and higher effect of preventing, ameliorating or treating a prion disease.

The anti-prion activity of the maleic acid salt and of the pharmaceutical composition of the present invention in terms of $IC_{50}$ (50% inhibitory concentration) as determined described later is preferably an $IC_{50}$ value of 1.0 µM or less, more preferably an $IC_{50}$ value of 0.5 µM or less, and further preferably an $IC_{50}$ value of 0.4 µM or less. The term "$IC_{50}$" herein refers to, when the concentration of prion protein measured in the absence of the maleic acid salt taken as 100%, the effective concentration of the maleic acid salt required to inhibit the prion protein by 50%.

The present invention also includes an industrially advantageous novel method for producing the maleic acid salt of the present invention, the method comprising bringing the compound represented by formula (1) below into contact with maleic acid. The production method is disclosed herein in a sufficient manner so as to enable a person skilled in the art to carry it out to obtain the maleic acid salt described above.

(1)

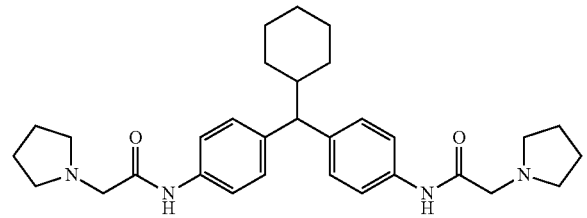

EXAMPLES

The present invention will be specifically described with reference to Examples and Comparative Examples, but the present invention is not limited thereto.

Production of Organic Acid Salts

Example 1

Under an argon atmosphere, 890 g (9.5 mol) of aniline was mixed with 270 g (2.4 mol) of cyclohexanecarboxaldehyde. Then, 22.7 g (0.24 mol) of concentrated hydrochloric acid was added dropwise to the mixture at room temperature. The reaction mixture was heated to reflux at 140° C. for 5 hours. To the reaction mixture were added 1.1 kg of diethylene glycol and 10 g of an aqueous sodium hydroxide solution. Excess aniline was distilled away. The reaction mixture was subjected to extraction with 2.6 kg of 2 N hydrochloric acid and washed with 1.4 L of toluene. To the aqueous layer, a 5% aqueous sodium hydroxide solution was added. The precipitated crystals were collected and dried in vacuum to give 257 g of crude crystals A (yield: 38%, mp: 104 to 107° C.)

The $^1H$ nuclear magnetic resonance spectrum of crude crystals A is shown below.

Crude Crystals a $^1H$ NMR (CDCl$_3$, δ) 7.00 (d, 4H, Ar—H), 6.58 (d, 4H, Ar—H), 4.12 (d, 1H, CH), 1.95-1.93 (m, 1H, CH), 1.63 (m, 4H, CH$_2$), 1.18-1.15 (m, 4H, CH$_2$), 0.83 (q, 2H, CH$_2$)

The NMR analysis revealed that crude crystals A were 4,4'-(cyclohexylmethylene)dianiline.

Under an argon atmosphere, 257 g (0.92 mol) of crude crystals A were dissolved in 2.6 L of dichloromethane. To the mixture, 204 g (2.0 mol) of triethylamine was added. Then, 227 g (2.0 mol) of chloroacetyl chloride was added dropwise to the mixture under ice cooling. The mixture was stirred for 18 hours. The precipitated crystals were collected, washed with dichloromethane, and recrystallized in a mixture of THF/CPME to give 283 g of crystals B (yield: 71%, mp: 228° C.)

In 2.8 L of THF was dissolved 204 g (2.87 mol) of pyrrolidine, and to this, 283 g (0.65 mol) of crystals B were added in divided portions at room temperature. The mixture was stirred for 19 hours. The reaction mixture was subjected to extraction with 6.0 L of ethyl acetate, and washed with 3.4 L of ion exchanged water. The organic layer was washed with saturated brine and concentrated in vacuum to give crude crystals. The crude crystals were recrystallized in a mixture of THF/diisopropyl ether to give 274 g of crystals of N,N'-[(cyclohexylmethylene)di-4,1-phenylene]bis[2-(1-pyrrolidinyl)acetamide] (yield: 83%, mp: 167° C.)

The $^1H$ nuclear magnetic resonance spectrum of crystals B is shown below.

Crystals B $^1H$ NMR (CDCl$_3$, δ) 8.14 (br, 2H, CH$_2$), 7.41 (d, 4H, Ar—H), 7.24 (d, 4H, Ar—H), 4.16 (s, 4H, CH$_2$Cl), 3.46 (d, 1H, CH), 2.04 (q, 1H, CH), 1.57-1.55 (m, 4H, CH$_2$), 1.22-1.14 (m, 4H, CH$_2$), 0.85 (q, 2H, CH$_2$)

The NMR analysis revealed that crystals B were N,N'-[(cyclohexylmethylene)di-4,1-phenylene]bis(2-chloroacetamide).

The $^1H$ nuclear magnetic resonance spectrum of N,N'-[(cyclohexylmethylene)di-4,1-phenylene]bis[2-(1-pyrrolidinyl)acetamide] is shown below.

N,N'-[(cyclohexylmethylene)di-4,1-phenylene]bis[2-(1-pyrrolidinyl)acetamide]

$^1H$ NMR (CDCl$_3$, δ) 8.99 (br, 2H, NH), 7.45 (d, 4H, Ar—H), 7.21 (d, 4H, Ar—H), 3.43 (d, 1H, CH), 3.24 (s, 4H, C(O)CH$_2$), 2.67 (br, 8H, NCH$_2$), 2.08-2.00 (m, 1H, CH), 1.83 (quint, 8H, CH$_2$), 1.67-1.59 (m, 4H, CH$_2$), 1.24-1.12 (m, 4H, CH$_2$), 0.84 (q, 2H, CH$_2$)

In 2.0 L of THF was dissolved 100 g (0.2 mol) of N,N'-[(cyclohexylmethylene)di-4,1-phenylene]bis[2-(1-pyrrolidinyl)acetamide]. A solution of 51 g (0.43 mol) of maleic acid in THF (300 mL) was added dropwise to the solution under ice cooling. After completion of the addition, the mixture was stirred at room temperature for hours. The precipitated crystals were collected and recrystallized in a mixture of ethanol/ion exchanged water (30:1) to give 130.8 g of the compound of interest, N,N'-[(cyclohexylmethylene)di-4,1-phenylene]bis[2-(1-pyrrolidinyl)acetamide] maleate (yield: 89.5%, mp: 145.1° C.).

The $^1$H nuclear magnetic resonance spectrum (internal reference: TMS) of N,N'-[(cyclohexylmethylene)di-4,1-phenylene]bis[2-(1-pyrrolidinyl)acetamide] maleate is shown below.

N,N'-[(cyclohexylmethylene)di-4,1-phenylene]bis[2-(1-pyrrolidinyl) acetamide] maleate $^1$H NMR (dmso-d6, δ) 10.38 (br, 2H, NH), 7.45 (d, 4H, Ar—H), 7.30 (d, 4H, Ar—H), 6.02 (s, 4H, CH), 4.14 (s, 4H, C(O)CH$_2$), 3.47 (d, 1H, CH), 3.30 (br, 8H, NCH$_2$), 2.13-2.10 (m, 1H, CH), 1.93 (quint, 8H, CH$_2$), 1.59 (m, 3H, CH$_2$), 1.46-1.43 (m, 2H, CH$_2$), 1.19-1.13 (m, 3H, CH$_2$), 0.84-0.78 (q, 2H, CH$_2$)

Neutralization titration indicated that this maleic acid salt was formed by binding of two molecules of maleic acid. To confirm that the maleic acid salt was a dimaleate salt (molecular formula: $C_{39}H_{50}N_4O_{10}$), elemental analysis was performed and the results are shown below. The difference between the calculated values and the measured values was within ±0.3%. The analysis results confirmed that the maleic acid salt was formed by binding of two molecules of maleic acid.

Calculated Values: C, 63.75%; H, 6.86%; N, 7.62%
Measured Values: C, 63.48%; H, 6.89%; N, 7.48%

Comparative Example 1

In 2.0 L of THF was dissolved 100 g (0.198 mol) of N,N'-[(cyclohexylmethylene)di-4,1-phenylene]bis[2-(1-pyrrolidinyl)acetamide] obtained above. A solution of 51.4 g (0.435 mmol) of succinic acid in 0.9 L of THF was added dropwise to the solution under ice cooling. After completion of the addition, the mixture was stirred at room temperature for 24 hours. The precipitated crystals were collected and recrystallized in THF to give 74.2 g of the compound of interest, N,N'-[(cyclohexylmethylene)di-4,1-phenylene]bis[2-(1-pyrrolidinyl)acetamide] succinate (yield: 50.5%, mp: 145° C.)

The $^1$H nuclear magnetic resonance spectrum of N,N'-[(cyclohexylmethylene)di-4,1-phenylene]bis[2-(1-pyrrolidinyl)acetamide] succinate is shown below.

N,N'-[(cyclohexylmethylene)di-4,1-phenylene]bis[2-(1-pyrrolidinyl)acetamide] succinate $^1$H NMR (CDCl$_3$, δ) 9.18 (br, 2H, NH), 7.45 (d, 4H, Ar—H), 7.19 (d, 4H, Ar—H), 3.72 (d, 1H, CH), 2.78 (s, 4H, C(O)CH$_2$), 2.58 (br, 8H, NCH$_2$), 2.07-2.04 (m, 1H, CH), 1.88 (quint, 8H, CH$_2$), 1.65-1.57 (m, 5H, CH$_2$), 1.23-1.15 (m, 3H, CH$_2$), 0.86-0.83 (m, 2H, CH$_2$)

Screening of Organic Acid Salts in Terms of Crystallinity

Test Example 1

Various types of acid addition salts were produced in the same manner as in Example 1 except that the type of the acid addition salt produced was changed from a maleic acid salt to a hydrochloric acid salt, a sulfuric acid salt, a phosphoric acid salt, a citric acid salt, a malic acid salt, a tartaric acid salt, an acetic acid salt, a lactic acid salt, a salicylic acid salt, a mandelic acid salt, a fumaric acid salt or a benzenesulfonic acid salt, that the synthesis of the acid addition salt was run at 1/100 scale of Example 1, and that the solvent for recrystallization was changed to the solvents shown in Table 1. The crystallinity of the salts was then evaluated. In addition to these salts, also evaluated were the maleic acid salt of Example 1 produced at 1/100 scale and the succinic acid salt of Comparative Example 1 produced at 1/100 scale. Table 1 shows the results of screening. The acetic acid salt, the succinic acid salt and the maleic acid salt were selected as candidates. Synthesis of these candidates was scaled up to the same scale as in Example 1. In the scale-up synthesis of the acetic acid salt, however, acetic acid was liberated, i.e., released from the salt during drying and, as a result, the acetic acid salt was not obtained.

TABLE 1

Crystallinity of organic acid salts

| Acid | Solvent | | | | | | | |
|---|---|---|---|---|---|---|---|---|
| | Methanol | Ethanol | 1-propanol | Isopropanol | 1-pentanol | Acetone | Acetonitrile | THF |
| Hydrochloric acid | D | D | D | D | D | D | D | D |
| Sulfuric acid | D | D | D | D | D | D | D | D |
| Phosphoric acid | D | C | C | C | C | C | C | C |
| Citric acid | D | C | C | B | B | C | C | C |
| Malic acid | D | D | D | C | C | C | B | D |
| Succinic acid | D | D | D | D | D | D | B | A |
| Tartaric acid | D | C | B | C | C | C | C | B |
| Acetic acid | D | D | D | B or A | D | D | B | D |
| Lactic acid | D | D | D | B | D | D | B | D |
| Salicylic acid | D | D | D | D | D | D | D | D |
| Maleic acid | D | A | D | D | D | D | D | B |
| Mandelic acid | D | B | D | B | D | B | B | D |
| Fumaric acid | D | D | D | C | D | B | D | D |
| Benzenesulfonic acid | D | D | D | B | D | B | D | B |

A: favorable crystalline formation.
B: crystals were obtained.
C: precipitate was observed.
D: no crystal formation or precipitation.

Stress Testing on Organic Acid Salts

Example 2

The crystals of N,N'-[(cyclohexylmethylene)di-4,1-phenylene]bis[2-(1-pyrrolidinyl)acetamide] maleate produced in Example 1 were placed in a petri dish. The petri dish was placed in a constant temperature and humidity chamber at 40±2° C. with a humidity of 75±5% for 2 weeks to perform stress testing. The maleic acid salt after the stress testing was observed. FIG. 1 shows the photograph of the maleic acid salt after the two-week stress testing.

The maleic acid salt after the two-week stress testing retained its original white crystalline powder form, indicating that the maleic acid salt of the present invention has high crystallinity and high stability in the crystalline form. The stress testing was further continued at the same temperature and conditions. The maleic acid salt after one-month stress testing also retained its original white crystalline powder form.

Comparative Example 2

Figure 2:
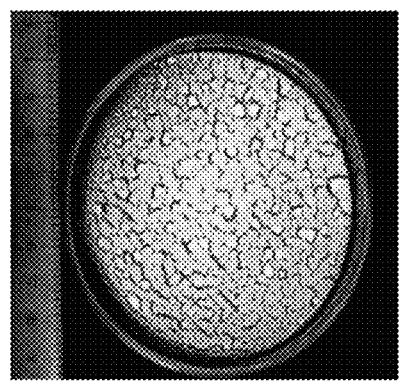
FIG. 2 shows a photograph of a succinic acid salt after two-week stress testing in Comparative Example 2.

The crystals of N,N'-[(cyclohexylmethylene)di-4,1-phenylene]bis[2-(1-pyrrolidinyl)acetamide] succinate produced in Comparative Example 1 were placed in a petri dish. The petri dish was placed in a constant temperature and humidity chamber at 40±2° C. with a humidity of 75±5% for 2 weeks to perform stress testing. The succinic acid salt after the stress testing was observed. FIG. 2 shows the photograph of the succinic acid salt after the two-week stress testing.

The succinic acid salt after the two-week stress testing turned into a thick, sticky liquid and failed to maintain their original powder form, indicating that the succinic acid salt has high moisture-absorbing properties and has lower crystallinity and lower stability than the maleic acid salt tested in Example 2. The stress testing was further continued at the same temperature and conditions, and the succinic acid salt after one-month stress testing was obtained.

Example 3

X-ray diffraction analysis was performed on the maleic acid salt (the maleic acid salt produced in Example 1) in a conventional manner using an X-ray diffractometer (product name: D8 ADVANCE) under the conditions described below before stress testing and after the two-week and one-month stress testing.
X-ray: Cu Kα radiation (1.54 angstroms)
Target: Cu
X-ray tube current: 45 mA
X-ray tube voltage: 45 kV
Scanning range: 2θ=4.000 to 70.134°
Step: 2θ=0.021°

Figure 3:
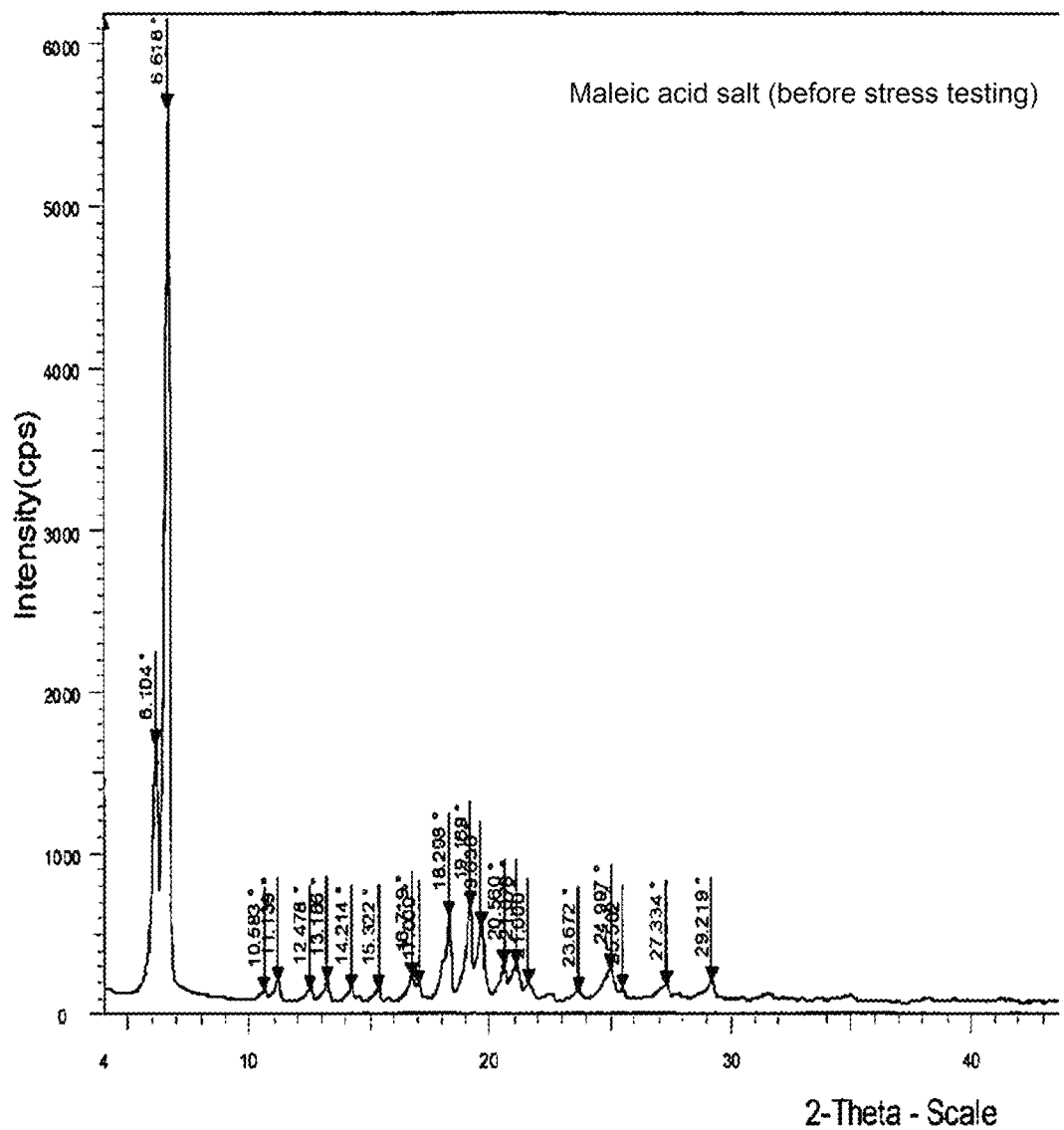
FIG. 3 shows an X-ray diffraction chart of a maleic acid salt before stress testing in Example 3.
Figure 4:
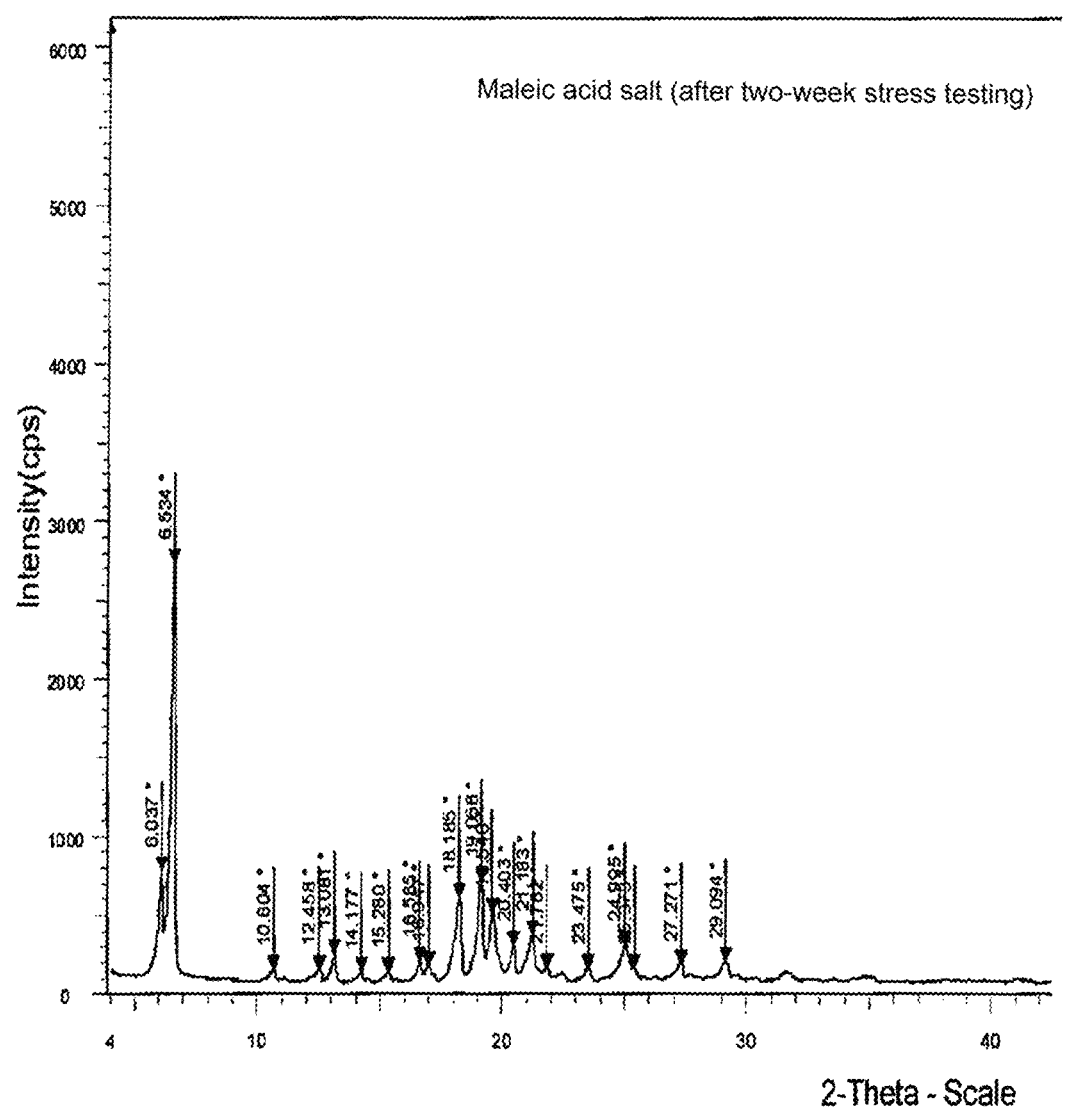
FIG. 4 shows an X-ray diffraction chart of a maleic acid salt after two-week stress testing in Example 3.
Figure 5:
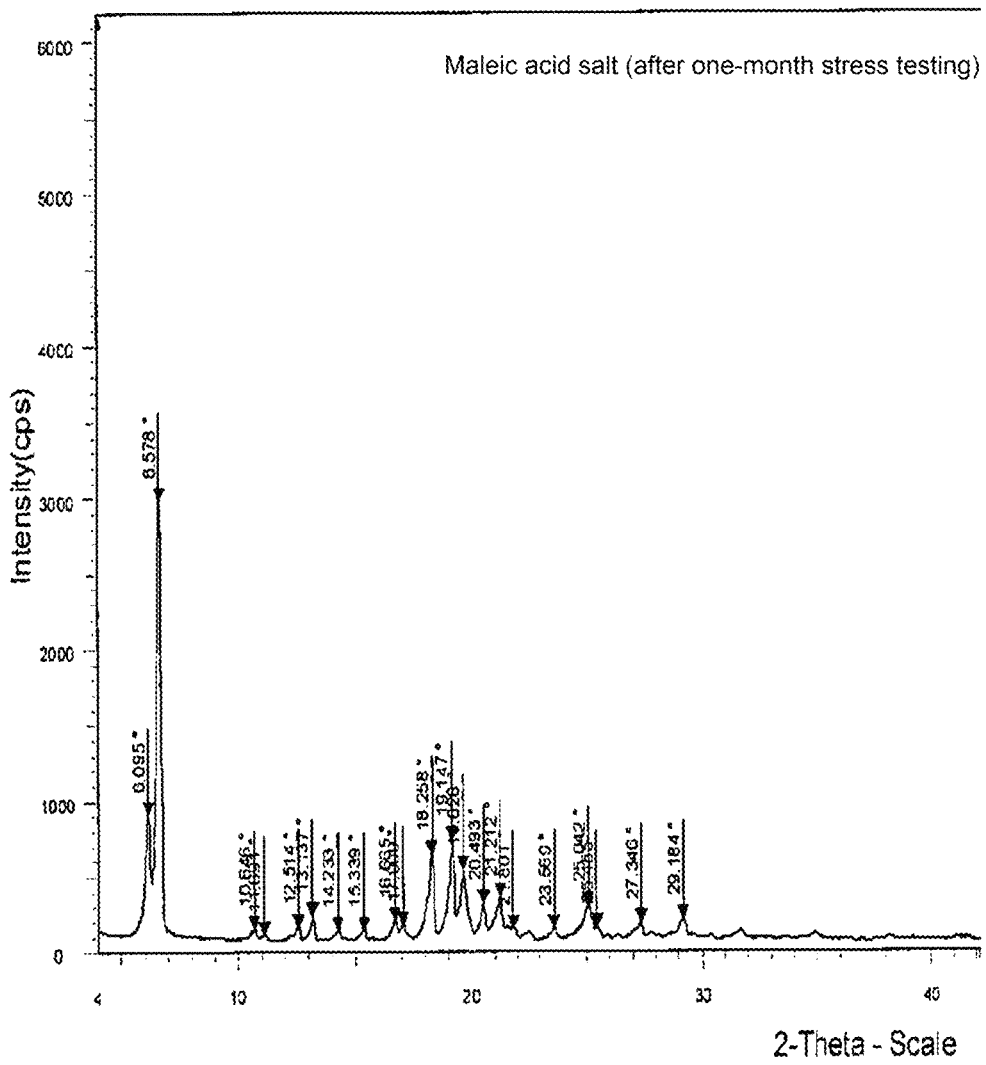
FIG. 5 shows an X-ray diffraction chart of a maleic acid salt after one-month stress testing in Example 3.

FIGS. 3, 4 and 5 show the measurement results of the maleic acid salt before stress testing and after the two-week and one-month stress testing, respectively. In FIGS. 3 to 5, the term "Intensity" refers to the diffraction intensity, and the term "2-Theta-Scale" refers to the diffraction angle (2θ(°)). The results in the figures show that the X-ray diffraction patterns from the maleic acid salt remained the same before stress testing and after the two-week and one-month stress testing, indicating that the maleic acid salt is very stable in the crystalline form. The results thus revealed that the maleic acid salt of the present invention has high crystallinity and is stable in the crystalline form.

Comparative Example 3

Figure 6:
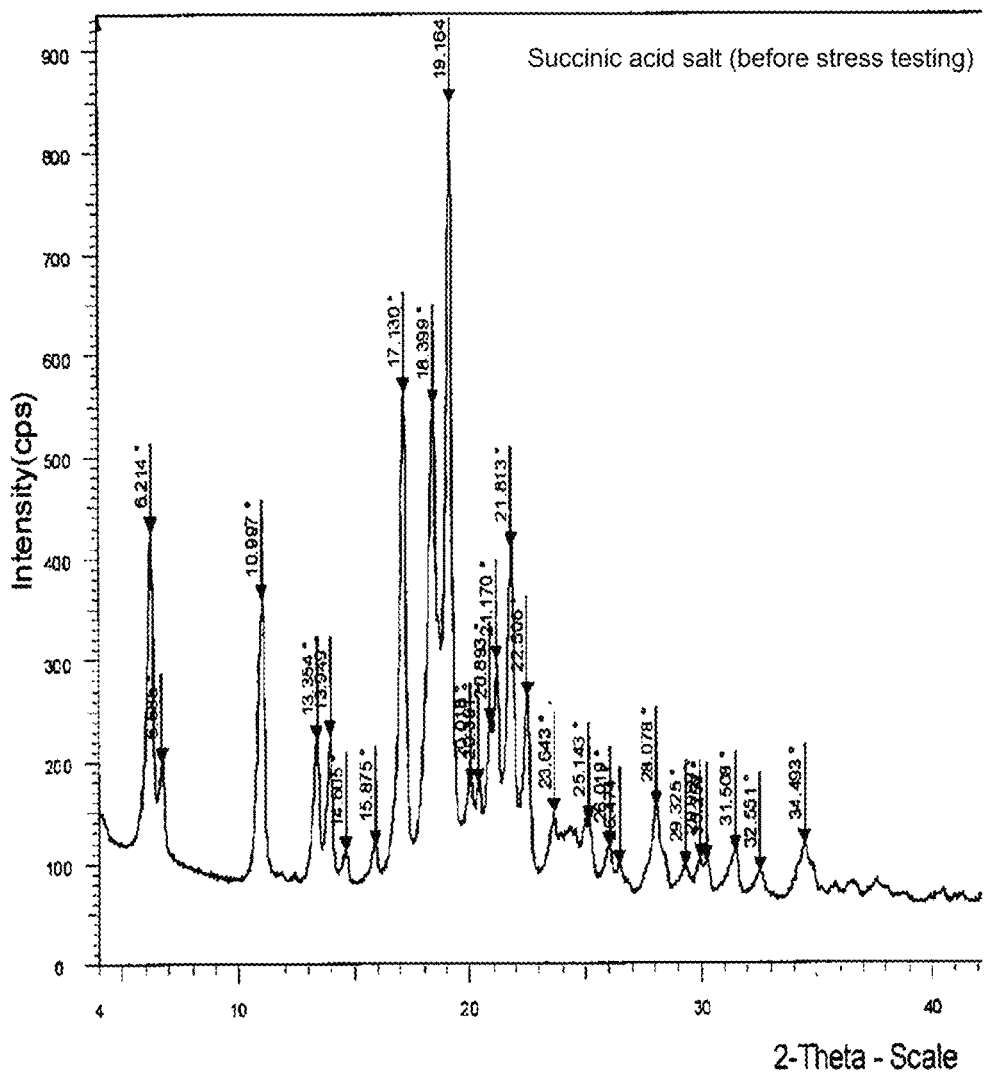
FIG. 6 shows an X-ray diffraction chart of a succinic acid salt before stress testing in Comparative Example 3.
Figure 7:
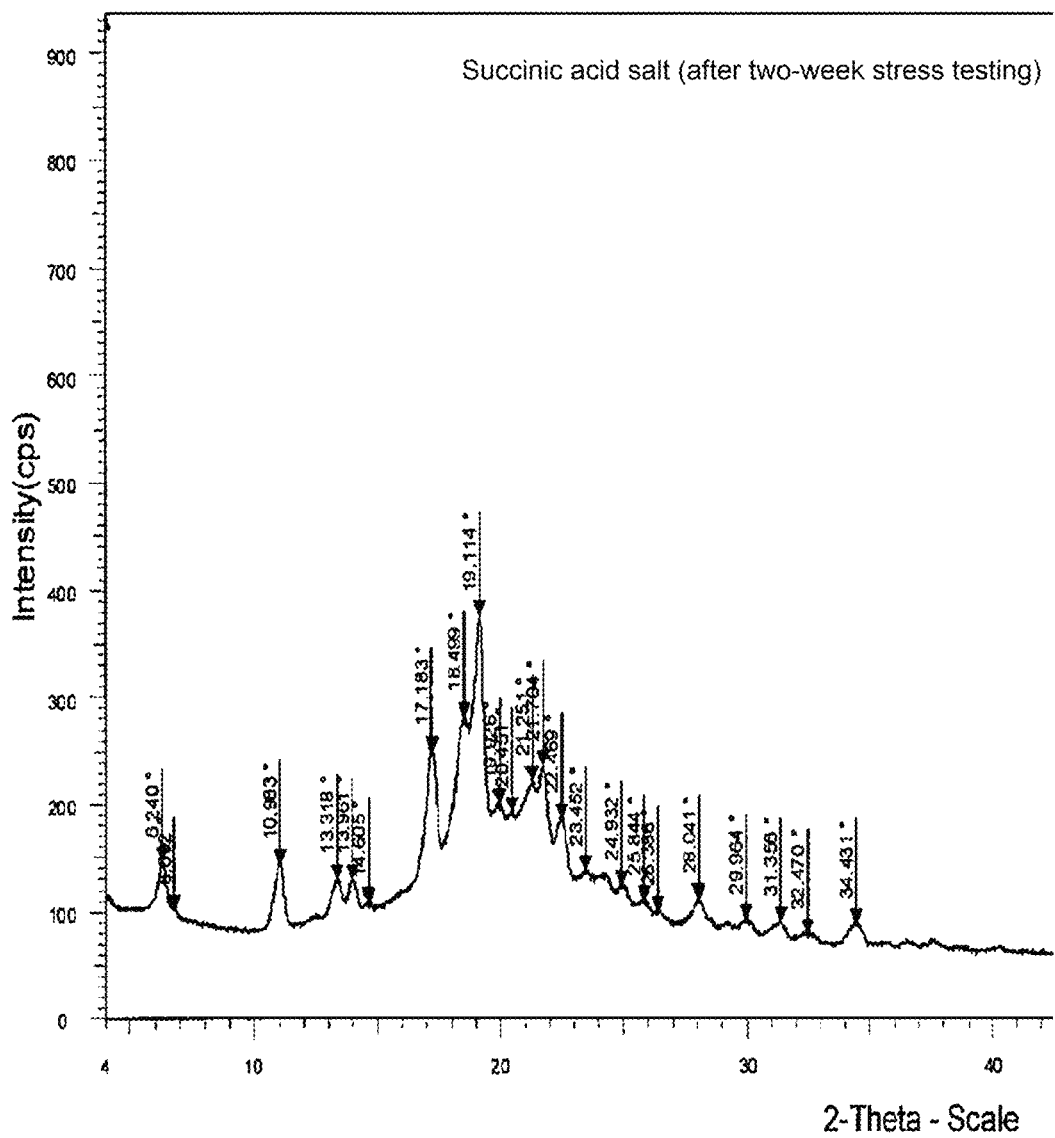
FIG. 7 shows an X-ray diffraction chart of a succinic acid salt after two-week stress testing in Comparative Example 3.
Figure 8:
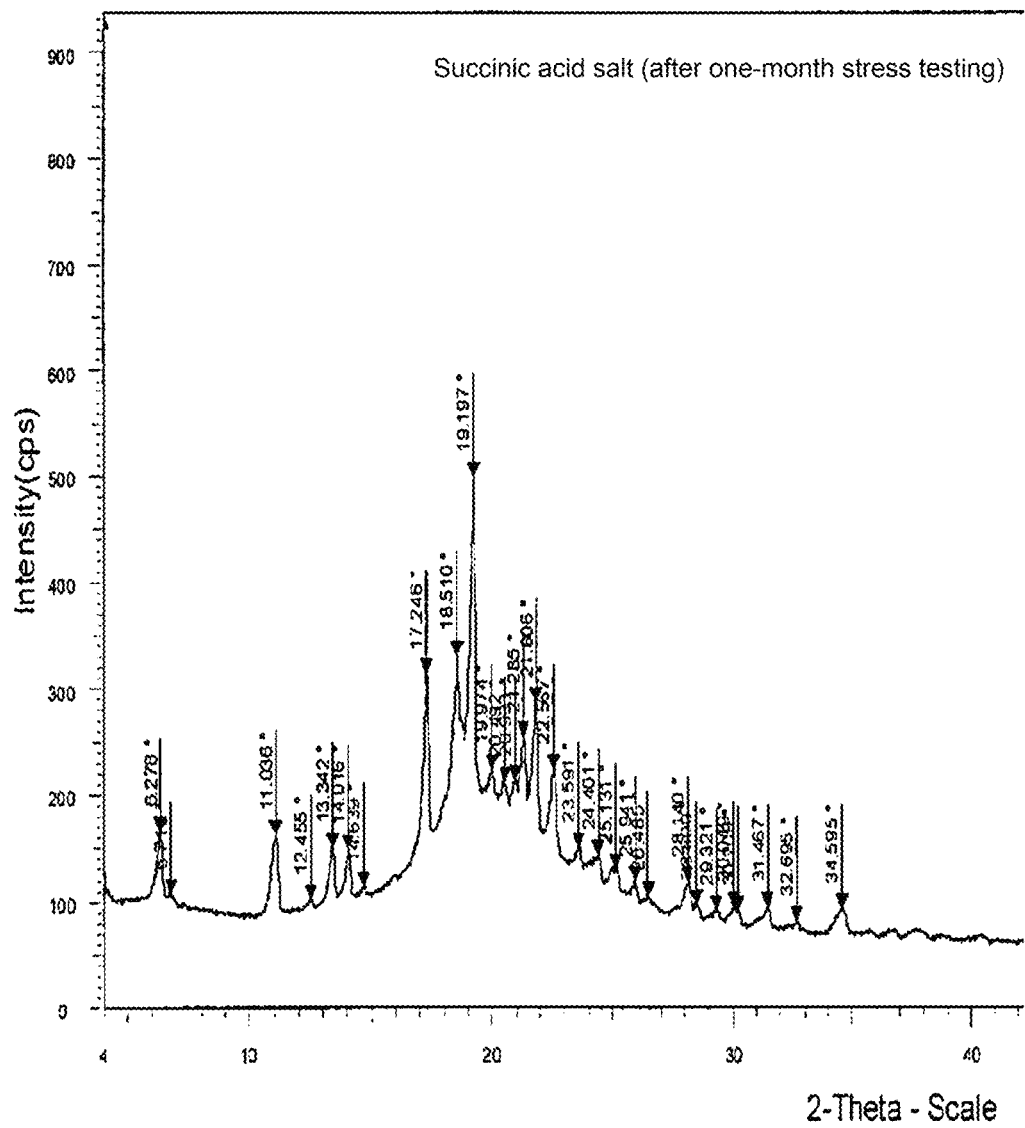
FIG. 8 shows an X-ray diffraction chart of a succinic acid salt after one-month stress testing in Comparative Example 3.

X-ray diffraction analysis was performed on the succinic acid salt (the succinic acid salt produced in Comparative Example 1) in the same manner as in Example 3 using an X-ray diffractometer before stress testing and after the two-week and one-month stress testing. FIGS. 6, 7 and 8 show the measurement results of the succinic acid salt before stress testing and after the two-week and one-month stress testing, respectively. In FIGS. 6 to 8, the term "Intensity" refers to the diffraction intensity, and the term "2-Theta-Scale" refers to the diffraction angle (2θ(°)). The results in the figures show that the X-ray diffraction patterns from the succinic acid salt measured after the two-week and one-month stress testing were different from that measured before the stress testing, indicating that the succinic acid salt is unstable in the crystalline form.

The overall results showed that the maleic acid salt of the present invention surprisingly has the most excellent crystallinity and stability. In addition to the finding, it was also discovered that the maleic acid salt has significantly more excellent crystallinity and stability than the free form of the compound.

Administration Testing

Test Example 2

N,N'-[(cyclohexylmethylene)di-4,1-phenylene]bis[2-(1-pyrrolidinyl)acetamide] maleate produced in Example 1 was dissolved in physiological saline for injection to prepare a dosing solution at 50 mg/mL and pH 3.79. The preparation of the dosing solution was performed under UV-cut fluorescent light on the day of administration.

The prepared dosing solution was administered to cynomolgus monkeys (males and females at 3 to 5 years old with a body weight of 3 to 4 kg) as test animals by oral gavage into the stomach using a gastric tube connected to a disposable syringe (single administration). The dose of the solution was 5 mL/kg and calculated based on the body weight measured on the day of administration. At 1, 2, 4, 8 and 24 hours after administration, about 0.5 mL of the blood was collected per time point from the cephalic vein or saphenous vein using heparin (sodium salt) as an anticoagulant.

The blood was centrifuged (at about 10,000×g at about 4° C. for 3 minutes) to give the plasma of the individual animals. The concentration of N,N'-[(cyclohexylmethylene)di-4,1-phenylene]bis[2-(1-pyrrolidinyl)acetamide] maleate in the plasma was measured by HPLC. The results are shown in Table 2. In table 2, the term "BLQ" indicates a concentration below the limit of quantification (<5 ng/mL). The results revealed that the maleic acid salt of the present invention is resistant to degradation and highly stable in the blood.

TABLE 2

Plasma concentrations of the maleic acid salt (oral administration)

| Dose (mg/kg) | Test animal No. | Plasma concentration (ng/mL) | | | | |
|---|---|---|---|---|---|---|
| | | 1 h after administration | 2 h after administration | 4 h after administration | 8 h after administration | 24 h after administration |
| 250 | 10101 | 8.27 | 7.23 | 8.72 | BLQ | BLQ |
| | 50101 | 9.10 | 12.6 | 11.7 | 6.39 | BLQ |
| | Mean | 8.69 | 9.92 | 10.2 | BLQ | BLQ |

Test Example 3

N,N'-[(cyclohexylmethylene)di-4,1-phenylene]bis[2-(1-pyrrolidinyl)acetamide] maleate produced in Example 1 was dissolved in physiological saline for injection to prepare dosing solutions at 12.5 mg/mL and 0.2 mg/mL. The preparation of the dosing solutions were performed under UV-cut fluorescent light on the day of administration. The dosing solution at 12.5 mg/mL had a pH of 3.74, and the dosing solution at 0.2 mg/mL had a pH of 4.47.

Each of the two types of dosing solutions was intravenously administered to cynomolgus monkeys (females at 3 to 5 years old with a body weight of 2 to 4 kg) as test animals via the saphenous vein at a rate of 0.5 mL/min or 2 mL/min using a disposable syringe with an injection needle (24 G) (single administration). At 5 minutes and 2, 4, 8 and 24 hours after administration, about 0.5 mL of the blood was collected per time point from the cephalic vein or saphenous vein. The doses of the solutions were calculated based on the body weight measured on the day of administration. As an anticoagulant, heparin (sodium salt) was used.

The blood was centrifuged (at about 10,000×g at about 4° C. for 3 minutes) to give the plasma of the individual animals. The concentration of N,N'-[(cyclohexylmethylene)di-4,1-phenylene]bis[2-(1-pyrrolidinyl)acetamide] maleate in the plasma was measured by HPLC. The results are shown in Table 3. The results revealed that the maleic acid salt of the present invention is resistant to degradation and highly stable in the blood.

serum, U/mL penicillin G and 50 mg/mL streptomycin sulfate. After the cells reached confluence, the cells were passaged every 7 days using 0.25% trypsin and 1 mM EDTA (ethylenediaminetetraacetic acid). The concentration of the cells was adjusted to $0.5 \times 10^5$ cells/mL.

The maleic acid salt of Example 1 (N,N'-[(cyclohexylmethylene)di-4,1-phenylene]bis[2-(1-pyrrolidinyl)acetamide] maleate) was dissolved in DMSO at a concentration of 10 mM. About $3 \times 10^5$ cells were seeded in each well of a 6-well plate, and the culture medium was replaced with fresh culture medium containing the maleic acid salt every 24 hours. As a control, culture medium containing DMSO at the same concentration was used. Three days after the addition of the maleic acid salt, the cells were lysed with 150 μL of Triton-DOC lysis buffer. After the lysate was centrifuged at 11,200×g, the concentration of protein in the supernatant was measured by BCA Protein Assay Kit (Pierce), and the lysate was adjusted to 1 mg/mL with the lysis buffer to give a sample.

The sample was hydrolyzed with 20 μg/mL proteinase K at 37° C. for 30 minutes, and then the reaction was stopped with a 3 mM inhibitor (Pefabloc). The sample was centrifuged at 21,952×g at 4° C. for 45 minutes, and the pellet was dissolved in a sample buffer and boiled. The solution was electrophoresed on a 15% polyacrylamide gel at 180 V for 20 minutes. For Western blot analysis, the protein was transferred to a PVDF membrane (Immobilon-P, Millipore). The primary antibody for detecting an abnormal isoform of prion protein was M-20 antibody (Santa Cruz Biotechnol-

TABLE 3

Plasma concentrations of the maleic acid salt (Intravenous administration)

| Dose (mg/kg) | Test animal No. | Plasma concentration (ng/mL) | | | | |
|---|---|---|---|---|---|---|
| | | 5 min after administration | 2 h after administration | 4 h after administration | 8 h after administration | 24 h after administration |
| 100 | 50201 | 2120 | 983 | 628 | 582 | 86.9 |
| 10 | 50301 | 161 | 33.2 | 19.1 | 9.85 | 5.57 |

Quantification of Abnormal Isoform of Prion Protein

Test Example 4

Mouse hypothalamic neuronal cell line GT1 has been reported to be susceptible to mouse prion. GTFK-1 cell line was used to assess the anti-prion effect of the maleic acid salt of the present invention (N. Nishida et al., J. Virol, 74, 320-325 (2000)). This cell line was a mouse-adapted prion Fukuoka-1 strain derived from a GSS patient (O. Milhavet et al., Proc. Natl. Acad. Sci. U.S.A., 97, 13937-13942 (2000)).

The GTFK cells were cultured at 37° C. under 5% $CO_2$ in Dulbecco's medium supplemented with 10% fetal bovine ogy). The signal was visualized with SuperSignal reagent (Pierce) and scanned with LAS-1000 UV image analyzer (LAS-1000 UV mini, FUJIFILM). The density of all the abnormal prion protein bands was measured, and a comparison of the band densities was performed using Multi Gauge (software application). The concentration of abnormal prion protein measured in the absence of the maleic acid salt of Example 1 was taken as 100%, and the effective concentration of the maleic acid salt required to inhibit abnormal prion protein by 50% ($IC_{50}$) was determined by varying the concentration of the maleic acid salt added to the cells (0.05, 0.1, 0.3, 0.5, 0.8, 1.2, 1.5, 2.0 and 5.0 μM). The maleic acid salt of Example 1 showed an $IC_{50}$ value as low as 0.46±0.20 μM, indicating that the maleic acid salt of the present invention is effective for the prevention, amelioration or treatment of a prion disease.

Pharmacokinetic Study after Single Administration in Rats

Test Example 5

To 29.9 mg of N,N'-[(cyclohexylmethylene)di-4,1-phenylene]bis[2-(1-pyrrolidinyl)acetamide] maleate produced in Example 1 was added 100 mL of physiological saline (Japanese pharmacopoeia) (Otsuka Pharmaceutical Factory). The mixture was stirred with a stirrer until dissolution of the maleic acid salt to give a solution at 0.2 mg/mL expressed in terms of N,N'-[(cyclohexylmethylene)di-4,1-phenylene]bis[2-(1-pyrrolidinyl)acetamide]. This solution was used as a dosing solution for bolus intravenous administration and oral administration. The dosing solution was filtered through a 0.22-µm filter and sterilized. Then, 60 mL of the solution was taken, and diluted by addition of 90 mL of physiological saline (Japanese pharmacopoeia) to give a dosing solution at 0.08 mg/mL (expressed in terms of N,N'-[(cyclohexylmethylene)di-4,1-phenylene]bis[2-(1-pyrrolidinyl)acetamide]) for continuous intravenous infusion. The preparation of the dosing solutions was performed under UV-cut fluorescent light on the day of administration. The pH of the two types of dosing solutions was 4.68.

Male Crl:CD (SD) rats at 8 weeks old were purchased (from Charles River Laboratories Japan). The animals were maintained at 19.0 to 25.0° C. with a relative humidity of 35.0 to 75.0% under a 12-hour light cycle (7:00 to 19:00). The animals had free access to solid feed (CR-LPF, sterilized by irradiation, Oriental Yeast) and water (tap water filtered through a 5-µm filter followed by UV irradiation). From the start of feeding, the general conditions of each animal were observed daily for 5 days or longer, and the animals in good health were placed in quarantine. The body weights of the animals were measured on the day of the arrival and at the end of the quarantine period, and increase in the body weights indicated steady growth of the animals. The body weights of the animals at the end of the quarantine period was within ±20% of the mean body weight. After the end of the quarantine period, acclimation and daily monitoring of the general conditions were continued until the day of administration (immediately before administration) of the dosing solution.

Bolus intravenous administration was performed as follows. The dosing solution was administered (at a single dose) to the rats that were quarantined and acclimated (at 8 weeks old at the time of administration) via the tail vein at a rate of 1 mL/min using a disposable syringe (2.5 mL, TERUMO) with a butterfly injection needle (25 G×¾, NIPRO). The dose of the solution was calculated based on the body weight measured on the day of administration and was determined to be 1 mg/kg.

Continuous intravenous infusion was performed as follows. The dosing solution was administered (at a single dose) to the rats that were quarantined and acclimated (at 8 weeks old at the time of administration) via a catheter inserted into the femoral vein at a rate of 5.43 mL/kg·h using a disposable syringe (50 mL, TERUMO) connected to a syringe pump (TE-312, TERUMO). The rate of administration was calculated based on the body weight measured on the day of administration. Immediately before the administration, the catheter was flushed with physiological saline to clean the line. At the end of the administration, to prevent blood coagulation in the catheter, the catheter was filled with heparin/glycerol solution (a solution prepared by adding 4 volumes of heparin sodium injection solution (1,000 units) to 6 volumes of glycerol (final heparin sodium concentration: 400 units/mL), followed by filter sterilization and storage in a refrigerator). The dose of the solution was calculated based on the body weight measured on the day of administration and was determined to be 10 mg/kg.

Oral administration was performed as follows. The dosing solution was administered (at a single dose) to the rats that were quarantined and acclimated (at 8 weeks old at the time of administration) via oral gavage using a gastric tube (Fuchigami Kikai) connected to a disposable syringe (2.5 mL, TERUMO) loaded with the dosing solution in an amount equal to the sum of the dose and the dead volume of the syringe. The dose of the solution was calculated based on the body weight measured on the day of administration and was determined to be 1 mg/kg.

The dose of the solution in the bolus intravenous administration, the continuous intravenous infusion and the oral administration is expressed in terms of the amount of N,N'-[(cyclohexylmethylene)di-4,1-phenylene]bis[2-(1-pyrrolidinyl)acetamide].

At 5 minutes and 2, 4, 8, 24 and 48 hours after the end of the bolus intravenous administration, the continuous intravenous infusion or the oral administration, the blood was collected from the subclavian vein without anesthesia using an injection needle-equipped syringe treated with heparin sodium. The amount of the blood collected was about 0.25 mL (in the case of the blood collected within 8 hours after administration) or about 0.45 mL (in the case of the blood collected 24 hours or more after administration). The blood was transferred to micro test tubes. From the test tubes, 0.05 mL (in the case of the blood collected within 8 hours after administration) or 0.1 mL (in the case of the blood collected 24 hours or more after administration) was taken and placed in a sample holder with a Combusto-Pad (each n=1). The radioactivity was measured by the method described later to determine the concentrations of radioactivity in the blood. The remainder of the blood was centrifuged in a centrifuge (CF15D2, Hitachi Koki) (at 4° C., 12,000 rpm×5 min) to give the plasma. From the plasma, 0.05 mL (in the case of the blood collected within 8 hours after administration) or 0.1 mL (in the case of the blood collected 24 hours or more after administration) was taken and placed in a sample holder with a Combusto-Pad (each n=1). The radioactivity was measured by the method described later to determine the concentrations of radioactivity in the plasma. The results of the concentrations of radioactivity in the blood and plasma are shown in Table 4 and FIG. 9.

The time course of the concentrations of radioactivity in the blood and plasma was also analyzed by non-compartmental analysis using the pharmacokinetic analysis software, Phoenix WinNonlin 6.3 (Pharsight Corporation as part of Certara) to calculate the pharmacokinetic parameters. The results are also shown in Table 4.

Figure 9:
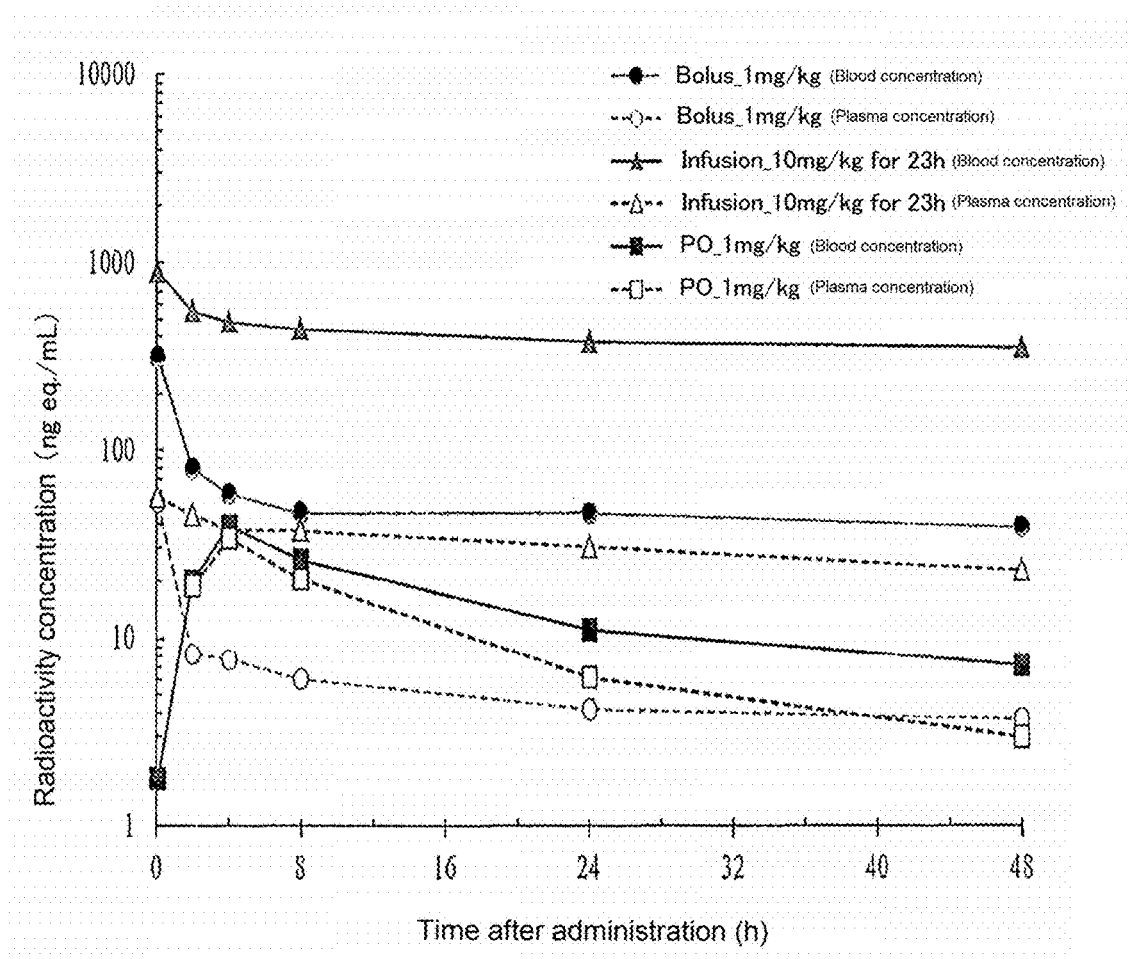
FIG. 9 shows the concentrations of radioactivity in blood and plasma after single administration of a maleic acid salt to rats in Test Example 5.

In Table 4 and FIG. 9, the term "Bolus" refers to bolus intravenous administration, the term "Infusion" refers to continuous intravenous infusion, and the term "PO" refers to oral administration.

Measurement of Radioactivity

The radioactivity was measured using a liquid scintillation counter (Tri-Carb 2300TR, PerkinElmer) with quench correction by the tSIE (transformed Spectral Index of External standard) method. Only a single measurement was conducted for each vial for 5 minutes. Background radioactivity was determined by 5-minute single measurement of a vial containing a scintillation cocktail alone that was the same as that for sample analysis or of a background vial prepared by combusting a Combusto-Pad (PerkinElmer).

The net counts were calculated by subtracting the background value from the measured value. The detection limit of radioactivity was set at twice the background value.

Before the measurement of the radioactivity of the samples that were combusted in a sample oxidizer (Model: 307, PerkinElmer), the recovery of a radionuclide (n=3, acceptable limit: 90.0% or more) was determined. After the final combustion, the recovery of a radionuclide (n=3) was also determined in the same manner as above. The combustion process in the sample oxidizer was performed by collecting the generated $^{14}CO_2$ with a $CO_2$ absorber (Carbo-Sorb (PerkinElmer) in an amount of 6 mL) and then mixing the $CO_2$ absorber with Permafluor E+ ((PerkinElmer) in an amount of 9 mL). The blood and the plasma were subjected to combustion in the sample oxidizer.

The concentrations of radioactivity in the blood and plasma were calculated from the radioactivity values as determined above using the pharmacokinetic study supporting system, ADMESUPPORT Ver 2.1 (FUJITSU). The following information was entered in the system: the information on the groups, the information on the nuclear species, the information on the purchased animals, the information on the dosing, the information on the sample collection and the information on the measurement schedule.

The concentrations of radioactivity in the blood and plasma were calculated in terms of the concentration of the free form of the maleic acid salt produced in Example 1 (N,N'-[(cyclohexylmethylene)di-4,1-phenylene]bis[2-(1-pyrrolidinyl)acetamide]).

TABLE 4

Radioactivity concentrations and pharmacokinetic parameters in blood and plasma after single administration of the maleic acid salt to rats

| | | Radioactivity concentration (ng eq./mL) | | | | | |
|---|---|---|---|---|---|---|---|
| | | Blood | | | Plasma | | |
| Time after administration, pharmacokinetic parameters | | Bolus (1 mg/kg) | Infusion (10 mg/kg for 23 h) | PO (1 mg/kg) | Bolus (1 mg/kg) | Infusion (10 mg/kg for 23 h) | PO (1 mg/kg) |
| | 5 min | 312.7 | 897.8 | 1.8 | 52.1 | 56.2 | ND |
| | 2 h | 79.2 | 554.0 | 20.4 | 8.2 | 44.6 | 19.0 |
| | 4 h | 57.6 | 477.4 | 39.5 | 7.6 | 37.4 | 33.8 |
| | 8 h | 45.3 | 445.7 | 26.0 | 6.0 | 37.0 | 20.5 |
| | 24 h | 45.6 | 376.6 | 11.1 | 4.2 | 30.6 | 6.2 |
| | 48 h | 38.5 | 348.2 | 7.1 | 3.7 | 22.8 | 3.0 |
| $C_{max}$ (ng eq./mL) | Maximum radioactivity concentration in blood or plasma | — | — | 39.5 | — | — | 33.8 |
| $t_{max}$ (h) | Time required to reach maximum radioactivity concentration in blood or plasma | — | — | 4.0 | — | — | 4.0 |
| $C_0$ (ng eq./mL) | Initial radioactivity concentration in plasma determined by extrapolation to time zero | 331.1 | — | — | 56.3 | — | — |
| $t_{1/2}$ (h) | Time required for concentration to fall to half | 98.8 | 99.3 | 18.7 | 46.1 | 62.2 | 12.9 |
| $AUC_{0-t}$ (ng eq. · h/mL) | Area under blood or plasma radioactivity concentration-time curve | 2424 | 19527 | 706 | 268 | 1500 | 472 |
| $AUC_{0-inf}$ (ng eq. · h/mL) | Area under blood or plasma radioactivity concentration-time curve | 7956 | 69626 | 896 | 514 | 3562 | 527 |
| $CL_{total}$ (mL/h · g) | Total systemic clearance | 128 | 145 | — | 1947 | 2845 | — |
| $CL_{total}/F$ (mL/h · g) | Total apparent systemic clearance | — | — | 1120 | — | — | 1969 |
| $Vd_{ss}$ (mL/kg) | Volume of distribution at steady state | 17445 | 19037 | — | 125155 | 214311 | — |
| $Vd_z/F$ (mL/kg) | Apparent terminal-phase volume of distribution | — | — | 30263 | — | — | 36594 |
| $MRT_{0-inf}$ (h) | Mean residence time | 138.4 | 132.1 | 30.3 | 64.4 | 77.6 | 20.6 |
| Fa (%) | Fraction absorbed | — | — | 11.3 | — | — | 102.5 |

$t_{1/2}$ was calculated using the concentrations from 4 h to 48 h.
ND: Not detected
—: Not applicable
Fa = ($AUC_{0-inf}$ PO)/($AUC_{0-inf}$ Bolus) × 100

The results in Table 4 and FIG. 9 showed that the blood concentrations of radioactivity were consistently 6- to 11-fold higher than the plasma concentrations of radioactivity from 5 minutes after administration to 48 hours after administration in the bolus intravenous administration to the rats, indicating that the maleic acid salt of the present invention has high distribution to blood cells.

The blood concentrations of radioactivity were also consistently 12- to 16-fold higher than the plasma concentrations of radioactivity in the continuous intravenous infusion.

The overall results indicated that the maleic acid salt of the present invention is particularly suitable for intravenous administration by injection.

Test Example 6

Measurement of Tissue Concentrations of Radioactivity

Table 6 shows the concentrations of radioactivity in tissues at 48 hours after single administration of the maleic acid salt of Example 1 to rats. Table 7 shows the percentage distribution to blood cells (T) and the ratio of the concentrations of radioactivity in blood to those in plasma ($R_B$). The concentrations of radioactivity in tissues, the percentage distribution to blood cells (T) and the ratio of the concentrations of radioactivity in blood to those in plasma ($R_B$) were determined as described below.

At 48 hours after the bolus intravenous administration, the continuous intravenous infusion or the oral administration, the rats underwent laparotomy under anesthesia by inhalation of isoflurane. The blood was taken as much as possible from the caudal vena cava. The rats were euthanized by cutting the abdominal aorta to allow bleeding to occur, and various tissues as indicated in Table 5 below were harvested. In Table 5, tissues A to D mean as follows: A. a whole organ was harvested and part of the harvested organ was subjected to radioactivity measurement, B. a whole organ was harvested and the whole of the harvested organ was subjected to radioactivity measurement, C. part of an organ was harvested and part of the harvested partial organ was subjected to radioactivity measurement, and D. part of an organ was harvested and the whole of the harvested partial organ was subjected to radioactivity measurement.

TABLE 5

Harvested samples

| — | Blood | B | Thymus | B | Pancreas |
|---|---|---|---|---|---|
| — | Plasma | B | Heart | B | Testis |
| B | Cerebrum | B | Lung | D | Mesenteric lymph nodes |
| B | Cerebellum | A | Liver | C | Skeletal muscle (thigh muscle) |
| B | Pituitary | B | Kidney | C | Bone (femur) |
| B | Submaxillary gland | B | Adrenal | C | White adipose tissue (periphery of testis) |
| B | Thyroid | B | Spleen | — | Cerebrospinal fluid |

The concentrations of radioactivity in the harvested tissues were measured in the same manner as in Test Example 5.

One milliliter of the blood sample was placed in a sample holder with a Combusto-Pad (n=1) to determine the concentration of radioactivity in the blood in the same manner as in Test Example 5. Part of the blood sample was taken up in a capillary tube (n=1), and centrifuged (at 12,000 rpm×5 minutes) in a centrifuge (HC-12A, TOMY SEIKO) to determine the hematocrit value. The remainder of the blood sample was centrifuged (at 4° C., 3,000 rpm×10 minutes) in a centrifuge (CF7D2, Hitachi Koki), and the plasma was collected from the supernatant. An aliquot of 1 mL from the plasma was taken and placed in a sample holder with a Combusto-Pad (n=1) to determine the concentration of radioactivity in the plasma in the same manner as in Test Example 5.

The ratio of the concentrations of radioactivity in the tissues to those in the plasma (T/P ratio) was also calculated. The percentage distribution of radioactivity to blood cells (T) and the ratio of the concentrations of radioactivity in the blood to those in the plasma ($R_B$) were calculated from the concentrations of radioactivity in the blood ($C_b$), the concentrations of radioactivity in the plasma ($C_p$) and the hematocrit values ($H_t$) in accordance with the formulae shown below. For the calculation of the T/P ratio, and the T and $R_B$ values, Microsoft Excel 2010 (Microsoft Corporation) was used. The T and $R_B$ values are determined by the following formulae.

$$T(\%) = (1 - C_p/C_b \times (100 - H_t)/100) \times 100$$

$$R_B = C_b/C_p$$

The harvested tissues were classified into A to D. The tissues were washed with physiological saline, and remaining moisture was removed with a piece of filter paper. The tissues were then treated as follows.

Tissue A: The weight of the tissue was measured, and the tissue was cut into small pieces with dissecting scissors. About 0.5 g of the tissue pieces was weighed into a sample holder with a Combusto-Pad (n=1), and the tissue was combusted in the sample oxidizer.

Tissue B: The tissue was weighed into a sample holder with a Combusto-Pad, and the whole was combusted in the sample oxidizer.

Tissue C: Part of the tissue was harvested. About 0.1 g was taken from the white adipose tissue (n=1) and about 0.3 g was taken from the other tissues (n=1). The weighed tissue was placed in a sample holder with a Combusto-Pad and combusted in the sample oxidizer.

Tissue D: Part of the tissue was weighed into a sample holder with a Combusto-Pad, and combusted in the sample oxidizer.

The cerebrospinal fluid sample was treated as follows. Part of the cerebrospinal fluid was taken with a Myjector syringe (TERUMO) and weighed into a sample holder with a Combusto-Pad (n=1), and the sample was combusted in the sample oxidizer.

TABLE 6

Tissue concentrations of radioactivity at 48 h after single administration of the maleic acid salt to rats

| Tissue | Bolus intravenous administration (1 mg/kg) | Continuous intravenous infusion (10 mg/kg for 23 h) | Oral administration (1 mg/kg) |
|---|---|---|---|
| Blood | 39.7 (10.18) | 407.9 (19.52) | 10.00 (4.55) |
| Plasma | 3.9 (1.00) | 20.9 (1.0) | 2.2 (1.00) |
| Cerebrum | 72.3 (18.54) | 292.1 (13.98) | 17.1 (7.77) |
| Cerebellum | 19.3 (4.95) | 295.7 (14.15) | 10.1 (4.59) |
| Pituitary | 4317.8 (1107.13) | 52196.9 (2497.46) | 385.4 (175.18) |
| Submaxillary gland | 2855.0 (732.05) | 27325.5 (1307.44) | 946.2 (430.09) |
| Mesenteric lymph nodes | 5855.8 (1501.49) | 69303.2 (3315.94) | 2152.7 (978.50) |
| Thyroid | 2951.7 (756.85) | 32876.4 (1573.03) | 738.3 (335.59) |
| Thymus | 1826.8 (468.41) | 14576.6 (697.44) | 278.2 (126.45) |
| Heart | 1102.7 (282.74) | 13746.9 (657.75) | 213.8 (97.18) |
| Lung | 8426.7 (2160.69) | 161436.4 (7724.3) | 1539.5 (699.77) |
| Liver | 3094.2 (793.38) | 37954.5 (1816.00) | 1312.2 (596.45) |
| Adrenal | 13870.9 (3556.64) | 95579.5 (4573.18) | 2366.3 (1075.59) |
| Kidney | 5296.4 (1358.05) | 62073.2 (2970.01) | 495.0 (225.00) |
| Spleen | 13562.1 (3477.46) | 201967.0 (9663.49) | 1230.7 (559.41) |
| Pancreas | 2137.0 (547.95) | 17592.2 (841.73) | 325.9 (148.14) |
| Testis | 62.1 (15.92) | 472.4 (22.60) | 16.2 (7.36) |
| Skeletal muscle | 518.6 (132.97) | 4084.8 (195.44) | 139.2 (63.27) |
| Bone | 712.9 (182.79) | 1502.5 (71.89) | 86.9 (39.50) |
| White adipose tissue | 179.7 (46.08) | 2390.7 (114.39) | 140.7 (63.95) |
| Cerebrospinal fluid | ND (NC) | 1.6 (0.08) | ND (NC) |

ND: Not detected (<0.7 ng eq./g)
NC: Not calculated

TABLE 7

Percentage distribution to blood cells and the ratio of concentrations of radioactivity in blood to those in plasma at 48 h after single administration of the maleic acid salt to rats

| Dosing route | Hematocrit value ($H_t$) | Radioactivity concentration (ng eq./mL) Blood ($C_b$) | Radioactivity concentration (ng eq./mL) Plasma ($C_p$) | Distribution to blood cells (T) (%) | Blood concentration of radioactivity/plasma concentration of radioactivity ($R_B$) |
|---|---|---|---|---|---|
| IV (bolus) | 36.0 | 39.7 | 3.9 | 93.7 | 10.18 |
| IV (Infusion) | 32.0 | 407.9 | 20.9 | 96.5 | 19.52 |
| PO | 36.5 | 10.0 | 2.2 | 86.0 | 4.55 |

As shown in Tables 6 and 7, 100-fold higher radioactivity than in the plasma was observed in the pituitary, submaxillary gland, mesenteric lymph nodes, thyroid, thymus, lung, liver, adrenal, kidney, spleen and pancreas at 48 hours after administration in all of the routes of administration. The results indicated that the maleic acid salt of the present invention has high distribution to tissues.

The concentrations of radioactivity in the cerebrum and cerebellum were higher than those in the blood, indicating that the maleic acid salt of the present invention also has high distribution to the central nervous system.

Pharmacokinetic Study after Single Administration in Cynomolgus Monkeys

Test Example 7

To 22.4 mg of N,N'-[(cyclohexylmethylene)di-4,1-phenylene]bis[2-(1-pyrrolidinyl)acetamide] maleate produced in Example 1 was added 15 mL of physiological saline (Japanese pharmacopoeia) (Otsuka Pharmaceutical Factory). The mixture was stirred with a stirrer until dissolution of the maleic acid salt. The solution was filtered through a 0.22-μm filter and then sterilized to give a dosing solution at 2.0 mg/mL (expressed in terms of N,N'-[(cyclohexylmethylene)di-4,1-phenylene]bis[2-(1-pyrrolidinyl)acetamide]). The preparation of the dosing solution was performed under UV-cut fluorescent light on the day of administration. The pH of the dosing solution was 3.969.

Cynomolgus monkeys were purchased (from Charles River Laboratories Japan (exporting country: China)). The monkeys were quarantined and acclimated in a facility designated for inspection of monkeys for 6 weeks including a post-import quarantine period of 30 days or longer. The animals in good health were transferred to an experimental room.

After transfer of the animals, the general conditions and the food intake were observed for 6 days to confirm that the animals were in good health, and the dosing solution was administered to the animals. The body weight of the cynomolgus monkeys at the time of administration was 3.60 to 4.34 kg.

The breeding environment was as follows. The animals had free access to solid feed (CMK-2, CLEA Japan) and drinking water (tap water filtered through a 5-μm filter followed by UV irradiation) at 23.0 to 29.0° C. with a relative humidity of 35.0 to 75.0% under a 12-hour light cycle (7:00 to 19:00).

Bolus intravenous administration was performed as follows. The dosing solution was administered (at a single dose) to the cynomolgus monkeys (at 4 years old at the time of administration) via the saphenous vein at a rate of 2 mL/min using a disposable syringe (2.5 mL, TERUMO) with a butterfly injection needle (25 G×¾", NIPRO). The dose of the solution was calculated based on the body weight measured on the day of administration and was determined to be 1 mg/kg.

The blood was collected from the cephalic vein or femoral vein without anesthesia at 5, 15 and 30 minutes, and 1, 2, 4, 8, 10, 24, 48, 72, 120 and 168 hours after the end of the bolus intravenous administration. The amount of the blood collected was about 0.50 mL (in the case of the blood collected within 120 hours after administration) or about 5 mL (in the case of the blood collected at 168 hours after administration). The concentrations of radioactivity in blood and plasma and the pharmacokinetic parameters were determined for each blood sample. The results are shown in Table 8 and FIG. 10.

The percentage distribution of radioactivity to blood cells (T) and the ratio of the concentrations of radioactivity in the blood to those in the plasma ($R_B$) were also determined in the same manner as in Test Example 6 at 1, 4 and 24 hours after the bolus intravenous administration, and the results are shown in Table 9.

TABLE 8

Radioactivity concentrations and pharmacokinetic parameters in blood and plasma after single bolus intravenous administration of the maleic acid salt to cynomolgus monkeys

| Time after administration, pharmacokinetic parameters | | Radioactivity concentration (ng eq./mL) | |
|---|---|---|---|
| | | Blood | Plasma |
| 5 min | | 632.2 | 320.0 |
| 15 min | | 300.1 | 167.9 |
| 30 min | | 217.7 | 134.4 |
| 1 h | | 190.3 | 113.4 |
| 2 h | | 143.8 | 99.3 |
| 4 h | | 122.2 | 77.3 |
| 8 h | | 107.2 | 68.7 |
| 10 h | | 96.9 | 58.9 |
| 24 h | | 61.4 | 52.8 |
| 48 h | | 56.5 | 48.4 |
| 72 h | | 47.5 | 48.3 |
| 120 h | | 43.3 | 36.6 |
| 168 h | | 36.9 | 34.9 |
| $C_0$ (ng eq./mL) | Initial radioactivity concentration in blood or plasma determined by extrapolation to time zero | 915.5 | 440.9 |
| $t_{1/2}$ (h) | Time required for concentration to fall to half | 199.6 | 223.3 |
| $AUC_{0-t}$ (ng eq. · h/mL) | Area under blood or plasma radioactivity concentration-time curve | 9280 | 7785 |
| $AUC_{0-inf}$ (ng eq. · h/mL) | Area under blood or plasma radioactivity concentration-time curve | 19908 | 19030 |
| $CL_{total}$ (mL/h · kg) | Total systemic clearance | 50 | 53 |
| $Vd_{ss}$ (mL/kg) | Volume of distribution at steady state | 13811 | 16780 |
| $MRT_{0-inf}$ (h) | Mean residence time | 274.9 | 319.3 |

TABLE 9

Percentage distribution to blood cells and the ratio of concentrations of radioactivity in blood to those in plasma at 1, 4 and 24 h after single bolus intravenous administration of the maleic acid salt to cynomolgus monkeys

| Time | Hematocrit value ($H_t$) (%) | Radioactivity concentration (ng eq./mL) | | Distribution to blood cells (T) (%) | Blood concentration of radioactivity/ plasma concentration of radioactivity ($R_B$) |
|---|---|---|---|---|---|
| | | Blood ($C_b$) | Plasma ($C_p$) | | |
| 1 h after administration | 44.0 | 170.9 | 101.5 | 66.7 | 1.68 |
| 4 h after administration | 40.0 | 126.0 | 63.4 | 69.8 | 1.99 |
| 24 h after administration | 36.0 | 62.9 | 46.6 | 52.6 | 1.35 |

Figure 10:
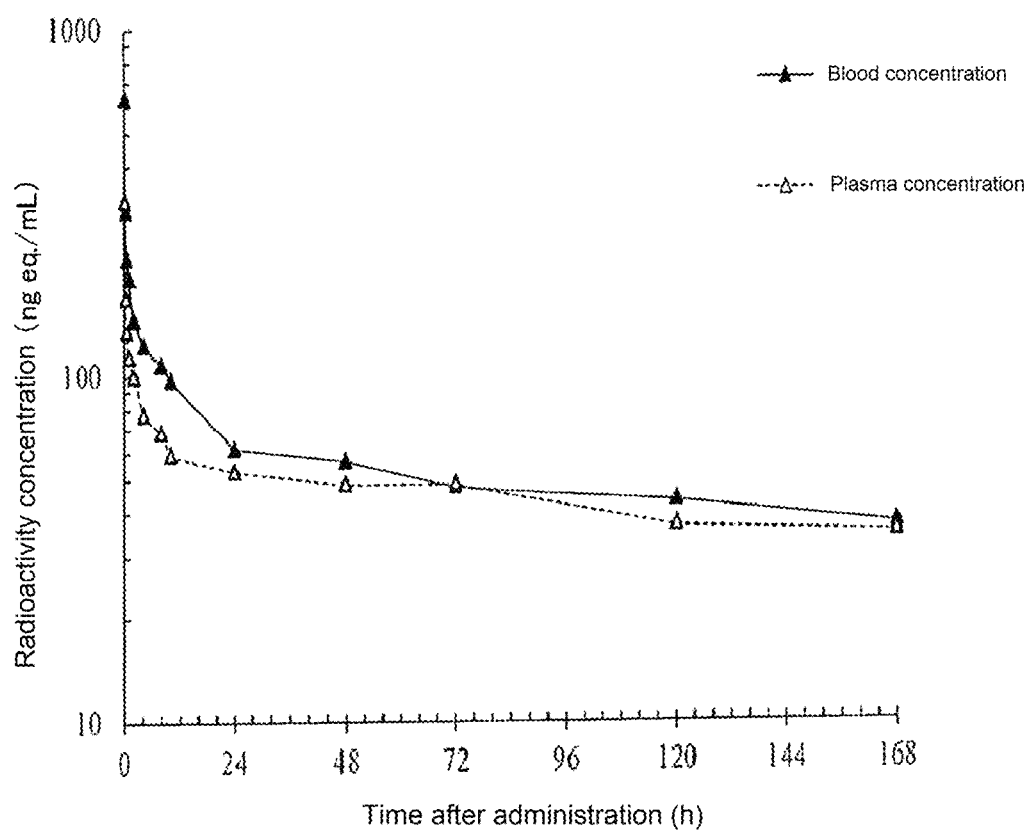
FIG. 10 shows the concentrations of radioactivity in blood and plasma after single bolus intravenous administration of a maleic acid salt to cynomolgus monkeys in Test Example 7.

The results in Tables 8 and 9 and FIG. 10 showed that, in the bolus intravenous administration to the cynomolgus monkeys, the blood concentrations of radioactivity relatively rapidly decreased from 5 minutes after administration to 24 hours after administration, and the radioactivity was slowly eliminated after 24 hours. The plasma concentrations of radioactivity were comparable or relatively lower than the blood concentrations of radioactivity. The results indicated that the maleic acid salt of the present invention mainly distributes to blood cells.

The overall results showed that the maleic acid salt of the present invention is suitable for intravenous administration by injection.

Test Example 8

Measurement of Tissue Concentrations of Radioactivity

To the cynomolgus monkeys from which the blood was collected at each time point in Test Example 7, pentobarbital (Somnopentyl, Kyoritsu Seiyaku) was intravenously administered at a dose of about 0.4 mL/kg, and the cynomolgus monkeys were euthanized by bloodletting from the carotid artery under the general anesthesia. Various tissues as indicated in Table 10 were harvested. In Table 10, the tissues were classified into A to C in the same manner as the classification in Table 5.

TABLE 10

| Harvested samples | | |
|---|---|---|
| — Blood | A Eyeballs | A Pancreas |
| — Plasma | A Submaxillary gland | A Testis |
| A Cerebral cortex | C Mesenteric lymph nodes | C Artery (abdominal aorta) |
| A Striatum | A Thyroid | C Skin (lower abdominal region, shaved) |
| A Hippocampus | A Thymus | C Skeletal muscle (thigh muscle) |
| A Hypothalamus | A Heart | C Bone marrow (femur) |
| A Cerebellum | A Lung | C White adipose tissue (periphery of testis) |
| A Medulla oblongata | A Liver | C Brown adipose tissue (armpit) |

TABLE 10-continued

Harvested samples

| | | |
|---|---|---|
| C Spinal cord | A Adrenal | A Gallbladder |
| — Cerebrospinal fluid | A Kidney | A Bile (from gallbladder) |
| A Stomach*[1] | A Spleen | B Pituitary |
| A Gastric contents*[1] | A Small intestine*[1] | A Large intestine*[1] (including cecum) |
| A Small intestinal contents*[1] | A Large intestinal contents*[1] (including cecum contents) | |

*[1]Samples were harvested only at 168 h after administration.

Collection of the blood and plasma samples for measurement of radioactivity was performed in the same manner as in Test Example 7.

The cerebrospinal fluid was collected with a Myjector syringe (27 G×½", 1 mL, TERUMO), and the radioactivity was measured in the same manner as in Test Example 6 to determine the concentrations of radioactivity in the cerebrospinal fluid.

The other tissues indicated in Table 10 were washed with physiological saline, and the remaining moisture was removed with a piece of filter paper.

The digestive tracts were dissected, and the contents were taken by washing the tracts twice with about 40 mL of physiological saline. The remaining moisture on the tracts was removed with a piece of filter paper. The saline solutions used in the washing performed twice were combined.

The bile was collected from the gallbladder with a syringe (TERUMO) coupled to an injection needle (TERUMO).

The radioactivity was measured for the collected samples in the same manner as in Test Example 6. For the tissues (except for the bile from the gallbladder and the contents of the digestive tracts), the tissue concentrations of radioactivity were determined. The ratio of the concentrations of radioactivity in the tissues to those in the plasma (T/P ratio) was also calculated. For the calculation of the T/P ratio, Microsoft Excel 2010 was used.

For the tissue samples of the whole organ of which the weight was measurable (tissues A and B), the percentage distribution of the administered radioactivity (the percentage distribution of radioactivity in tissues) was calculated based on the measured total weight of the organ. The percentage distributions of radioactivity to the blood, skeletal muscle, skin and white adipose tissue were calculated by setting the total weight of each organ at 6.0%, 41.4%, 9.4% and 7.8% of the body weight, respectively.

The harvested tissues were classified into A to C and treated as follows.

Tissue A: The weight of the tissue was measured, and the tissue was cut into small pieces with dissecting scissors. The contents of the digestive tracts (gastric contents, small intestinal contents and large intestinal contents) were crushed with a mixer. Part of the samples was weighed into a sample holder with a Combusto-Pad (n=1) and combusted in the sample oxidizer.

Tissue B: The tissue was weighed into a sample holder with a Combusto-Pad, and the whole was combusted in the sample oxidizer.

Tissue C: Part of the tissue was harvested, and about 0.1 g of the tissue was weighed into a sample holder with a Combusto-Pad (n=1) and combusted in the sample oxidizer.

The cerebrospinal fluid sample was treated as follows. Part of the cerebrospinal fluid was taken with a Myjector syringe (TERUMO) and weighed into a sample holder with a Combusto-Pad (n=1), and the sample was combusted in the sample oxidizer.

Tables 11 and 12 show the thus-determined concentrations of radioactivity in the tissues and the distribution of radioactivity in the tissues after the single bolus intravenous administration of the maleic acid salt of Example 1 to the cynomolgus monkeys at a dose of 1 mg/kg.

TABLE 11

Tissue concentrations of radioactivity at 1, 24 and 168 h after single bolus intravenous administration of the maleic acid salt to cynomolgus monkeys Radioactivity concentration (ng eq./mL)
(Tissue concentration of radioactivity/
plasma concentration of radioactivity
(T/P ratio))

| Tissue | 1 h after administration | 24 h after administration | 168 h after administration |
|---|---|---|---|
| Blood | 168.3 (1.87) | 62.9 (1.35) | 36.9 (1.06) |
| Plasma | 90.2 (1.00) | 46.6 (1.00) | 34.9 (1.00) |
| Cerebral cortex | 76.0 (0.84) | 75.2 (1.61) | 166.0 (4.76) |
| Striatum | 50.2 (0.56) | 73.0 (1.57) | 116.2 (3.33) |
| Hippocampus | 72.1 (0.80) | 68.4 (1.47) | 193.1 (5.53) |
| Hypothalamus | 303.6 (3.37) | 119.9 (2.57) | 246.8 (7.07) |
| Cerebellum | 87.1 (0.97) | 73.8 (1.58) | 187.2 (5.36) |
| Medulla oblongata | 56.3 (0.62) | 64.7 (1.39) | 154.3 (4.42) |
| Spinal cord | 25.1 (0.28) | 34.7 (0.74) | 87.1 (2.50) |
| Pituitary | 2924.5 (32.42) | 4161.5 (89.30) | 5785.9 (165.79) |
| Eyeballs | 80.6 (0.89) | 283.8 (6.09) | 370.0 (10.60) |
| Submaxillary gland | 2096.2 (23.24) | 2360.5 (50.65) | 3832.9 (109.83) |
| Mesenteric lymph nodes | 1526.5 (16.92) | 2270.0 (48.71) | 4501.3 (128.98) |
| Thyroid | 4815.7 (53.39) | 2417.3 (51.87) | 851.4 (24.40) |
| Thymus | 991.7 (10.99) | 7492.9 (160.79) | 2584.5 (74.05) |
| Heart | 7868.9 (87.24) | 4835.8 (103.77) | 1735.5 (49.73) |
| Lung | 16588.7 (183.91) | 12499.3 (268.23) | 12687.8 (363.55) |
| Liver | 7905.0 (87.64) | 541.02 (116.10) | 3961.6 (113.51) |
| Adrenal | 7381.2 (81.83) | 10530.4 (225.97) | 14988.5 (429.47) |

TABLE 11-continued

Tissue concentrations of radioactivity at 1, 24 and 168 h after single bolus intravenous administration of the maleic acid salt to cynomolgus monkeys Radioactivity concentration (ng eq./mL)
(Tissue concentration of radioactivity/plasma concentration of radioactivity (T/P ratio))

| Tissue | 1 h after administration | 24 h after administration | 168 h after administration |
|---|---|---|---|
| Kidney | 10277.2 (113.94) | 5524.9 (118.56) | 3965.6 (113.63) |
| Spleen | 7165.9 (79.44) | 10878.9 (233.45) | 14009.9 (401.43) |
| Pancreas | 4581.9 (50.80) | 4677.2 (100.37) | 7198.1 (206.25) |
| Testis | 331.0 (3.67) | 244.2 (5.24) | 775.9 (22.23) |
| Artery | 345.8 (3.83) | 232.8 (5.00) | 333.5 (9.56) |
| Skin | 239.4 (2.65) | 21.86 (4.69) | 327.6 (9.39) |
| Skeletal muscle | 1517.4 (16.82) | 1483.2 (31.83) | 521.8 (14.95) |
| Bone marrow | 223.8 (2.48) | 771.8 (16.56) | 863.1 (24.73) |
| White adipose tissue | 804.5 (8.92) | 220.4 (4.73) | 387.6 (11.11) |
| Brown adipose tissue | 7547.1 (83.67) | 9652.0 (207.13) | 9032.1 (258.80) |
| Gallbladder | 1271.6 (14.10) | 1795.1 (38.52) | 1112.6 (31.88) |
| Bile | 3488.0 (38.67) | 14772.6 (317.0) | 6306.0 (180.69) |
| Cerebrospinal fluid | 2.2 (0.02) | ND (NC) | ND (NC) |
| Stomach | — (—) | — (—) | 1190.1 (34.10) |
| Small intestine | — (—) | — (—) | 2740.2 (78.52) |
| Large intestine | — (—) | — (—) | 1167.0 (33.44) |

ND: Not detected
NC: Not calculated
—: Not applicable

TABLE 12

Percentage distribution of radioactivity in tissues at 1, 24 and 168 h after single bolus intravenous administration of the maleic acid salt to cynomolgus monkeys

| Tissue | Percentage distribution of radioactivity (relative to total radioactivity) (%) | | |
|---|---|---|---|
| | 1 h after administration | 24 h after administration | 168 h after administration |
| Blood | 0.98 | 0.38 | 0.23 |
| Cerebral cortex | 0.11 | 0.09 | 0.21 |
| Striatum | 0.00 | 0.01 | 0.01 |
| Hippocampus | 0.00 | 0.00 | 0.00 |
| Hypothalamus | 0.02 | 0.01 | 0.02 |
| Cerebellum | 0.01 | 0.01 | 0.03 |
| Medulla oblongata | 0.00 | 0.01 | 0.01 |
| Pituitary | 0.01 | 0.01 | 0.01 |
| Eyeballs | 0.01 | 0.06 | 0.05 |
| Submaxillary gland | 0.15 | 0.17 | 0.21 |
| Thyroid | 0.03 | 0.03 | 0.01 |
| Thymus | 0.03 | 0.12 | 0.11 |
| Heart | 2.32 | 1.45 | 0.60 |
| Lung | 8.08 | 5.35 | 4.43 |
| Liver | 13.35 | 9.93 | 5.48 |
| Adrenal | 0.11 | 0.20 | 0.20 |
| Kidney | 3.59 | 2.29 | 1.11 |
| Spleen | 0.80 | 0.79 | 0.98 |
| Pancreas | 0.69 | 0.92 | 1.06 |
| Testis | 0.09 | 0.14 | 0.21 |
| Skin | 2.18 | 2.07 | 3.15 |
| Skeletal muscle | 60.89 | 61.98 | 22.10 |
| White adipose tissue | 6.08 | 1.74 | 3.09 |
| Gallbladder | 0.01 | 0.01 | 0.01 |
| Bile | 0.27 | 0.68 | 0.28 |
| Stomach | — | — | 0.65 |
| Small intestine | — | — | 3.31 |
| Large intestine | — | — | 1.25 |
| Gastric contents | — | — | 0.03 |
| Small intestinal contents | — | — | 0.37 |
| Large intestinal contents | — | — | 2.01 |
| Total | 99.81 | 88.45 | 51.22 |

—: Not applicable

The results in Tables 11 and 12 showed that, in most of the tissues, the tissue concentrations of radioactivity were higher than the plasma concentrations of radioactivity, indicating that the maleic acid salt of the present invention has high distribution to tissues.

Many of the tissues including the adrenal, spleen, pancreas and pituitary showed the highest concentration at 168 hours after administration, and the amount of the radioactivity remaining in the body (the sum of the percentage distributions of radioactivity in the tissues) was 51.22% relative to the administered radioactivity. These results indicated that that the maleic acid salt of the present invention is highly retained in the tissues and is discharged from the body at a very slow rate.

Stability Testing in Aqueous Solution

Test Example 9

Reverse osmosis membrane (RO) water was produced using a reverse osmosis membrane (RO) water generator (Elix, Millipore) equipped with a filter (PROGARD S2 CARTRIDGE, Millipore).

In 2,000 mL of the reverse osmosis membrane (RO) water was dissolved 2 mL of trifluoroacetic acid (TFA) (Wako Special Grade, Wako Pure Chemical Industries) to prepare a 0.2% aqueous TFA solution. One volume of the 0.2% aqueous TFA solution was mixed with one volume of acetonitrile (acetonitrile for HPLC, Wako Pure Chemical Industries) with shaking to prepare a solution for dissolving a sample. Then, 5.0 mg of the maleic acid salt produced in Example 1 was weighed out and dissolved in the dissolving solution, and the volume was adjusted to 20 mL (25% w/v). The solution was stored in a 30-mL vial under either of two different temperature conditions: at room temperature (20° C.) and in a refrigerator (4° C.). The purity of the maleic acid salt was measured over time by taking 5 μL of the sample, subjecting the sample to liquid chromatography under the following conditions, and measuring the area of the peak of the maleic acid salt.

Measurement Conditions
 HPLC apparatus: Prominence (SHIMADZU)
 Detector: ultraviolet absorption spectrophotometer (measurement wavelength: 245 nm)
 Column: octadecylsilyl silica gel column (Inertsil ODS-2, GL Sciences)
 Column temperature: constant temperature of around 40° C.
 Mobile phase: start with 20:80 acetonitrile/0.2% TFA in water, linear gradient to 60:40 over 20 minutes, and then hold for 30 minutes.
 Flow rate: 1.0 mmL/min
 Injected sample solution: 5 μmL
 Under the above conditions, the maleic acid salt is detected around 15 minutes.

The purity of the maleic acid salt was determined from the following formula: (area of peak of maleic acid salt)/(sum of areas of peaks at retention time of between 4 to 35 minutes)× 100. The results are shown in Table 13.

The results in Table 13 revealed that the maleic acid salt of the present invention shows a retention rate of 97% or more even after 30-day storage in the form of an aqueous solution at room temperature or in a refrigerator, indicating that the maleic acid salt is stable even in the form of an aqueous solution.

TABLE 13

| Storage stability in aqueous solution | | |
|---|---|---|
| Storage conditions | Days of storage | Purity (%) |
| Room temperature (20° C.) | 0 | 98.77 |
| | 8 | 97.22 |
| | 17 | 98.16 |

TABLE 13-continued

| Storage stability in aqueous solution | | |
|---|---|---|
| Storage conditions | Days of storage | Purity (%) |
| | 22 | 98.08 |
| | 31 | 98.19 |
| Refrigerator (4° C.) | 0 | 98.77 |
| | 9 | 98.95 |
| | 18 | 99.23 |
| | 25 | 98.25 |
| | 32 | 97.88 |

INDUSTRIAL APPLICABILITY

The maleic acid salt of the present invention can be used as an active ingredient of a medicament for preventing, ameliorating or treating a prion disease. The maleic acid salt of the present invention has high crystallinity, is highly stable in the crystalline form, and can be synthesized at a large scale. Thus use of the maleic acid salt of the present invention enables the practical production of a medicament for preventing, ameliorating or treating a prion disease. The maleic acid salt of the present invention is soluble in water and can be formulated into an injection.

The invention claimed is:

1. A method for, ameliorating or treating a PrP prion disease, the method comprising administering the maleic acid salt of a compound represented by formula (1)

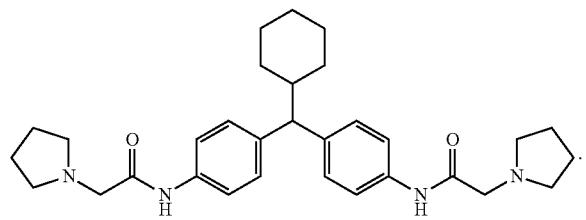

(1)

wherein the crystalline form has an X-ray diffraction pattern comprising characteristic peaks at:

| 2 Theta (Degrees) |
|---|
| 6.6 ± 0.1 |
| 10.6 ± 0.1 |
| 13.1 ± 0.1 |
| 14.2 ± 0.1 |
| 27.3 ± 0.1. |

2. The method of claim 1, wherein the administered maleic acid salt reaches the brain.

3. The method of claim 1 wherein the malic acid salt is administered by injection.

4. The method of claim 1 wherein the malic acid salt is administered intravenously.

* * * * *